United States Patent [19]
Rubinfeld et al.

[11] Patent Number: 5,948,643
[45] Date of Patent: Sep. 7, 1999

[54] MODULATORS OF BRCA1 ACTIVITY

[75] Inventors: Bonnee Rubinfeld, Danville; Paul G. Polakis, Mill Valley; Carol Lingenfelter; Terilyn T. Vuong, both of Oakland, all of Calif.

[73] Assignee: Onyx Pharmaceuticals, Inc., Richmond, Calif.

[21] Appl. No.: 08/968,751

[22] Filed: Aug. 13, 1997

[51] Int. Cl.⁶ .......................... C12P 21/06; C12N 15/00; C12N 5/00; C07H 21/02
[52] U.S. Cl. ..................... 435/69.1; 435/320.1; 435/325; 435/455; 536/23.1
[58] Field of Search .......................... 536/23.1; 435/69.1, 435/455, 320.1, 325

[56] References Cited

PUBLICATIONS

Chen et al., "BRCA1 is a 220–kDa Nuclear Phosphoprotein that is Expressed and Phosphorylated in a Cell Cycle–dependent Manner"—Cancer Research, pp. 3168–3172, Jul. 1996.

Chen et al., "The Nuclear Localization Sequences of the BRCA1 Protein Interact with the Importin–Subunit of the Nuclear Transport Signal"—The JBC, vol. 271, pp. 32863–32868, Dec. 1996.

Wu et al., "Identification of a RING protein that can interact in vivo with the BRCA1 gene product" Nature Genetics, vol. 14, pp. 430–440, Dec. 1996.

Wang et al., "BRCA1 proteins are transported to the nucleus in the absence of serum and splice variants BRCA1a, BRCA1b are tyrosine phosphoproteins that associate with E2F, cyclins and cyclin dependent kinases"—Oncogene, vol. 15, pp. 143–157, 1997.

Chassin et al. Genbank, Accession Number: L06432, May 8, 1993.

Hilliler et al. Genbank, Accession Number: W17337, Apr. 29, 1996.

Hillier et al. Genband, Accession Number: R40580, May 22, 1995.

*Primary Examiner*—Paula K. Hutzell
*Assistant Examiner*—Lin Sun-Hoffman
*Attorney, Agent, or Firm*—Gregory Giotta

[57] ABSTRACT

Compositions of matter consisting of a family of related nucleotide sequences that encode proteins, termed BRCA1 Modulator Proteins, that bind to the tumor suppressor gene product BRCA1, and methods of using the nucleotide sequences and the proteins encoded thereby, to diagnose and/or treat disease where the BRCA1 Modulator Proteins have an apparent molecular weight of 45–97 kdaltons and are characterized by having at least one leucine zipper domain, and optionally a zinc finger domain.

7 Claims, 7 Drawing Sheets

Sequence: 091-21 A31 Calculated Molecular Weight = 56821.53    Estimated pI = 9.28

```
        GTG GAT CCC CCG GGC TGC AGG AAT TCG GCA CGA GCG GCA CGA GTA CGA AGC CGG ACC TGT AGC AGT
66
         V   D   P   P   G   C   R   N   S   A   R   A   A   R   V   R   S   R   T   C   S   S>

TTC TTT GGC TGC CTG GGC CCC TTG AGT CCA GCC ATC ATG CCT ATC CGT GCT CTG TGC ACT ATC TGC
132
         F   F   G   C   L   G   P   L   S   P   A   I   M   P   I   R   A   L   C   T   I   C>

TCC GAC TTC TTC GAT CAC TCC CGC GAC GTG GCC GCC ATC CAC TGC GGC CAC ACC TTC CAC TTG CAG
198
         S   D   F   F   D   H   S   R   D   V   A   A   I   H   C   G   H   T   F   H   L   Q>
                                            "zinc" finger motif
        TGC CTA ATT CAG TGG TTT GAG ACA GCA CCA AGT CGG ACC TGC CCA CAG TGC CGA ATC CAG GTT GGC
264
         C   L   I   Q   W   F   E   T   A   P   S   R   T   C   P   Q   C   R   I   Q   V   G>

AAA AGA ACC ATT ATC AAT AAG CTC TTC TTT GAT CTT GCC CAG GAG GAG GAG AAT GTC TTG GAT GCA
330
         K   R   T   I   I   N   K   L   F   F   D   L   A   Q   E   E   E   N   V   L   D   A>

GAA TTC TTA AAG AAT GAA CTG GAC AAT GTC AGA GCC CAG CTT TCC CAG AAA GAC AAG GAG AAA CGA
396
         E   F   L   K   N   E   L   D   N   V   R   A   Q   L   S   Q   K   D   K   E   K   R>

GAC AGC CAG GTC ATC ATC GAC ACT CTG CGG GAT ACG CTG GAA GAA CGC AAT GCT ACT GTG GTA TCT
462
         D   S   Q   V   I   I   D   T   L   R   D   T   L   E   E   R   N   A   T   V   V   S>

CTG CAG CAG GCC TTG GGC AAG GCC GAG ATG CTG TGC TCC ACA CTG AAA AAG CAG ATG AAG TAC TTA
528
         L   Q   Q   A   L   G   K   A   E   M   L   C   S   T   L   K   K   Q   M   K   Y   L>

GAG CAG CAG CAG GAT GAG ACC AAA CAA GCA CAA GAG GAG GCC CGC CGG CTC AGG AGC AAG ATG AAG
594
         E   Q   Q   Q   D   E   T   K   Q   A   Q   E   E   A   R   R   L   R   S   K   M   K>

ACC ATG GAG CAG ATT GAG CTT CTA CTC CAG AGC CAG CGC CCT GAG GTG GAG GAG ATG ATC CGA GAC
660
         T   M   E   Q   I   E   L   L   L   Q   S   Q   R   P   E   V   E   E   M   I   R   D>

ATG GGT GTG GGA CAG TCA GCG GTG GAA CAG CTG GCT GTG TAC TGT GTG TCT CTC AAG AAA GAG TAC
726
         M   G   V   G   Q   S   A   V   E   Q   L   A   V   Y   C   V   S   L   K   K   E   Y>

GAG AAT CTA AAA GAG GCA CGG AAG GCC TCA GGG GAG GTG GCT GAC AAG CTG AGG AAG GAT TTG TTT
792
         E   N   L   K   E   A   R   K   A   S   G   E   V   A   D   K   L   R   K   D   L   F>

TCC TCC AGA AGC AAG TTG CAG ACA GTC TAC TCT GAA TTG GAT CAG GCC AAG TTA GAA CTG AAG TCA
858
         S   S   R   S   K   L   Q   T   V   Y   S   E   L   D   Q   A   K   L   E   L   K   S>
                                            leucine zipper motif
        GCC CAG AAG GAC TTA CAG AGT GCT GAC AAG GAA ATC ATG AGC CTG AAA AAG AAG CTA ACG ATG CTG
924
         A   Q   K   D   L   Q   S   A   D   K   E   I   M   S   L   K   K   K   L   T   M   L>

CAG GAA ACC TTG AAC CTG CCA CCA GTG GCC AGT GAG ACT GTC GAC CGC CTG GTT TTA GAG AGC CCA
990
         Q   E   T   L   N   L   P   P   V   A   S   E   T   V   D   R   L   V   L   E   S   P>

GCC CCT GTG GAG GTG AAT CTG AAG CTC CGC CGG CCA TCC TTC CGT GAT GAT ATT GAT CTC AAT GCT
1056
         A   P   V   E   V   N   L   K   L   R   R   P   S   F   R   D   D   I   D   L   N   A>

ACC TTT GAT GTG GAT ACT CCC CCA GCC CGG CCC TCC AGC TCC CAG CAT GGT TAC TAC GAA AAA CTT
1122
         T   F   D   V   D   T   P   P   A   R   P   S   S   S   Q   H   G   Y   Y   E   K   L>

TGC CTA GAG AAG TCA CAC TCC CCA ATT CAG GAT GTC CCC AAG AAG ATA TGC AAA GGC CCC AGG AAG
1188
         C   L   E   K   S   H   S   P   I   Q   D   V   P   K   K   I   C   K   G   P   R   K>
```

FIGURE 1

```
      GAG TCC CAG CTC TCA CTG GGT GGC CAG AGC TGT GCA GGA GAG CCA GAT GAG GAA CTG GTT GGT GCC
1254
       E   S   Q   L   S   L   G   G   Q   S   C   A   G   E   P   D   E   E   L   V   G   A>

TTC CCT ATT TTT GTC CGG AAT GCC ATC CTA GGC CAG AAA CAG CCC AAG AGG CCC AGG TCA GAG TCC
1320
       F   P   I   F   V   R   N   A   I   L   G   Q   K   Q   P   K   R   P   R   S   E   S>

TCT TGC AGC AAA GAT GTG GTA AGG ACA GGC TTC GAT GGG CTC GGT GGC CGG ACA AAA TTC ATC CAG
1386
       S   C   S   K   D   V   V   R   T   G   F   D   G   L   G   G   R   T   K   F   I   Q>

CCT ACT GAC ACA GTC ATG ATC CGC CCA TTG CCT GTT AAG CCC AAG ACC AAG GTT AAG CAG AGG GTG
1452
       P   T   D   T   V   M   I   R   P   L   P   V   K   P   K   T   K   V   K   Q   R   V>

AGG GTG AAG ACA GTG CCT TCT CTC TTC CAG GCC AAG CTG GAC ACC TTC CTG TGG TCG TGA GAACAGTGAG
1512
       R   V   K   T   V   P   S   L   F   Q   A   K   L   D   T   F   L   W   S   *>
```
TCTGACCAATGGCCAGACACATGCCTGCAACTTGTAGGTCAAGGACTGTCCAGGCAGGGGTTTTGTGGACAGAGCCCCACTTTCGGGACCAGCCTGAGGT
GTAAGGGCAGACAAACAGGTGAGGGTGAGTGTGACACCCAGAGACTGCTCTTCCTGCCCTCACCCTGCCCCACTCCTACGACTGGGAGCTGACATGACCA
GCCCACTGATCCTGTCAGCAGGTCCTGCTCCTGTTGCCAGGCTCCTGTTTATAGCCATGATCAGATGTGGTCAGACTCTTTCTGGGCCTGGAGACCACGG
TCACTTGTTGACTGTCTCTGTGGACCAGAGTGCTTGAGGCATCTCAGGCAGCCTCAGCCCAAGCTTCTACCTGCCTTTGACTTGCTTCTAGGCATAGCCT
GGGCCAAGCAGGGTGGGGAATGGAGGATAGCATGGGATGTATGGAGAGGATGGAAGATTTTCATGTAAATAAAATTAAAAAAAAAAAAACAAAAAAAAA
AAAAAAAAAAAAAAAAAAAAAAAAAAAAAAAAAAAACTCGAG

FIGURE 1a

Sequence of 091-1F84 Calculated Molecular Weight = 96443.30     Estimated pI = 4.95

```
       GAA CTA GTG GAT CCC CCG GGC TGC AGG AAT TCG GCA CGA GAA AGC TTA TCC CTT CCC TCG ATG CTT
 66     E   L   V   D   P   P   G   C   R   N   S   A   R   E   S   L   S   L   P   S   M   L>

CGG GAT GCT GCA ATT GGC ACT ACC CCT TTC TCT ACT TGC TCG GTG GGG ACT TGG TTT ACT CCT TCA
132     R   D   A   A   I   G   T   T   P   F   S   T   C   S   V   G   T   W   F   T   P   S>

GCA CCA CAG GAA AAG AGT ACA AAC ACA TCC CAG ACA GGC CTG GTT GGC ACC AAG CAC AGT ACT TCT
198     A   P   Q   E   K   S   T   N   T   S   Q   T   G   L   V   G   T   K   H   S   T   S>

GAG ACA GAG CAG CTC CTG TGT GGC CGG CCT CCA GAT CTG ACT GCC TTG TCT CGA CAT GAC TTG GAA
264     E   T   E   Q   L   L   C   G   R   P   P   D   L   T   A   L   S   R   H   D   L   E>

GAT AAC CTG CTG AGC TCT CTT GTC ATT CTG GAG GTT CTC TCC CGC CAG CTT CGG GAC TGG AAG AGC
330     D   N   L   L   S   S   L   V   I   L   E   V   L   S   R   Q   L   R   D   W   K   S>
                                          leucine zipper motif CAG CTG GCT GTC CCT CAC CCA GAA ACC CAG GAC AGT AGC ACA CAG ACT GAC ACA TCT CAC AGT GGG
396     Q   L   A   V   P   H   P   E   T   Q   D   S   S   T   Q   T   D   T   S   H   S   G>

ATA ACT AAT AAA CTT CAG CAT CTT AAG GAG AGC CAT GAG ATG GGA CAG GCC CTA CAG CAG GCC AGA
462     I   T   N   K   L   Q   H   L   K   E   S   H   E   M   G   Q   A   L   Q   Q   A   R>

AAT GTC ATG CAA TCA TGG GTG CTT ATC TCT AAA GAG CTG ATA TCC TTG CTT CAC CTA TCC CTG TTG
528     N   V   M   Q   S   W   V   L   I   S   K   E   L   I   S   L   L   H   L   S   L   L>

CAT TTA GAA GAA GAT AAG ACT ACT GTG AGT CAG GAG TCT CGG CGT GCA GAA ACA TTG GTC TGT TGC
594     H   L   E   E   D   K   T   T   V   S   Q   E   S   R   R   A   E   T   L   V   C   C>

TGT TTT GAT TTG CTG AAG AAA TTG AGG GCA AAG CTC CAG AGC CTC AAA GCA GAA AGG GAG GAG GCA
660     C   F   D   L   L   K   K   L   R   A   K   L   Q   S   L   K   A   E   R   E   E   A>

AGG CAC AGA GAG GAA ATG GCT CTC AGA GGC AAG GAT GCG GCA GAG ATA GTG TTG GAG GCT TTC TGT
726     R   H   R   E   E   M   A   L   R   G   K   D   A   A   E   I   V   L   E   A   F   C>

GCA CAC GCC AGC CAG CGC ATC AGC CAG CTG GAA CAG GAC CTA GCA TCC ATG CGG GAA TTC AGA GGC
792     A   H   A   S   Q   R   I   S   Q   L   E   Q   D   L   A   S   M   R   E   F   R   G>

CTT CTG AAG GAT GCC CAG ACC CAA CTG GTA GGG CTT CAT GCC AAG CAA GAA GAG CTG GTT CAG CAG
858     L   L   K   D   A   Q   T   Q   L   V   G   L   H   A   K   Q   E   E   L   V   Q   Q>

ACA GTG AGT CTT ACT TCT ACC TTG CAA CAA GAC TGG AGG TCC ATG CAA CTG GAT TAT ACA ACA TGG
924     T   V   S   L   T   S   T   L   Q   Q   D   W   R   S   M   Q   L   D   Y   T   T   W>

ACA GCT TTG CTG AGT CGG TCC CGA CAA CTC ACA GAG AAA CTC ACA GTC AAG AGC CAG CAA GCC CTG
990     T   A   L   L   S   R   S   R   Q   L   T   E   K   L   T   V   K   S   Q   Q   A   L>

CAG GAA CGT GAT GTG GCA ATT GAG GAA AAG CAG GAG GTT TCT AGG GTG CTG GAA CAA GTC TCT GCC
1056    Q   E   R   D   V   A   I   E   E   K   Q   E   V   S   R   V   L   E   Q   V   S   A>

CAG TTA GAG GAG TGC AAA GGC CAA ACA GAA CAA CTG GAG TTG GAA AAC AGT CGT CTA GCA ACA GAT
1122    Q   L   E   E   C   K   G   Q   T   E   Q   L   E   L   E   N   S   R   L   A   T   D>

CTC CGG GCT CAG TTG CAG ATT CTG GCC AAC ATG GAC AGC CAG CTA AAA GAG CTA CAG AGT CAG CAT
1188    L   R   A   Q   L   Q   I   L   A   N   M   D   S   Q   L   K   E   L   Q   S   Q   H>
```

FIGURE 2

```
1254  ACC CAT TGT GCC CAG GAC CTG GCT ATG AAG GAT GAG TTA TTC TGC CAG CTT ACC CAG AGC AAT GAG
       T   H   C   A   Q   D   L   A   M   K   D   E   L   F   C   Q   L   T   Q   S   N   E>

1320  GAG CAG GCT GCT CAA TGG CAA AAG GAA GAG ATG GCA CTA AAA CAC ATG CAG GCA GAA CTG CAG CAG
       E   Q   A   A   Q   W   Q   K   E   E   M   A   L   K   H   M   Q   A   E   L   Q   Q>

1386  CAA CAA GCT GTC CTG GCC AAA GAG GTG CGG GAC CTG AAA GAG ACC TTG GAG TTT GCA GAC CAG GAG
       Q   Q   A   V   L   A   K   E   V   R   D   L   K   E   T   L   E   F   A   D   Q   E>

1452  AAT CAG GTT GCT CAC CTG GAG CTG GGT CAG GTT GAG TGT CAA TTG AAA ACC ACA CTG GAA GTG CTC
       N   Q   V   A   H   L   E   L   G   Q   V   E   C   Q   L   K   T   T   L   E   V   L>

1518  CGG GAG CGC AGC TTG CAG TGT GAG AAC CTC AAG GAC ACT GTA GAG AAC CTA ACG GCT AAA CTG GCC
       R   E   R   S   L   Q   C   E   N   L   K   D   T   V   E   N   L   T   A   K   L   A>

1584  AGC ACC ATA GCA GAT AAC CAG GAG CAA GAT CTG GAG AAA ACA CGG CAG TAC TCT CAA AAG CTA AGG
       S   T   I   A   D   N   Q   E   Q   D   L   E   K   T   R   Q   Y   S   Q   K   L   R>

1650  CTG CTG ACT GAG CAA CTA CAG AGC CTG ACT CTC TTT CTA CAG ACA AAA CTA AAG GAG AAG ACT GAA
       L   L   T   E   Q   L   Q   S   L   T   L   F   L   Q   T   K   L   K   E   K   T   E>

1716  CAA GAG ACC CTT CTG CTG AGT ACA GCC TGT CCT CCC ACC CAG GAA CAC CCT CTG CCT AAT GAC AGG
       Q   E   T   L   L   L   S   T   A   C   P   P   T   Q   E   H   P   L   P   N   D   R>

1782  ACC TTC CTG GGA AGC ATC TTG ACA GCA GTG GCA GAT GAA GAG CCA GAA TCA ACT CCT GTG CCC TTG
       T   F   L   G   S   I   L   T   A   V   A   D   E   E   P   E   S   T   P   V   P   L>

1848  CTT GGA AGT GAC AAG AGT GCT TTC ACC CGA GTA GCA TCA ATG GTT TCC CTT CAG CCC GCA GAG ACC
       L   G   S   D   K   S   A   F   T   R   V   A   S   M   V   S   L   Q   P   A   E   T>

1914  CCA GGC ATG GAG GAG AGC CTG GCA GAA ATG AGT ATT ATG ACT ACT GAG CTT CAG AGT CTT TGT TCC
       P   G   M   E   E   S   L   A   E   M   S   I   M   T   T   E   L   Q   S   L   C   S>

1980  CTG CTA CAA GAG TCT AAA GAA GAA GCC ATC AGG ACT CTG CAG CGA AAA ATT TGT GAG CTG CAA GTT
       L   L   Q   E   S   K   E   E   A   I   R   T   L   Q   R   K   I   C   E   L   Q   V>

2046  AGG CTG CAG GCC CAG GAA GAA CAG CAT CAG GAA GTC CAG AAG GCA AAA GAA GCA GAC ATA GAG AAG
       R   L   Q   A   Q   E   E   Q   H   Q   E   V   Q   K   A   K   E   A   D   I   E   K>

2112  CTG AAC CAG GCC TTG TGC TTG CGC TAC AAG AAT GAA AAG GAG CTC CAG GAA GTG ATA CAG CAG CAG
       L   N   Q   A   L   C   L   R   Y   K   N   E   K   E   L   Q   E   V   I   Q   Q   Q>

2178  AAT GAG AAG ATC CTA GAA CAG ATA GAC AAG AGT GGC GAG CTC ATA AGC CTT AGA GAG GAG GTG ACC
       N   E   K   I   L   E   Q   I   D   K   S   G   E   L   I   S   L   R   E   E   V   T>

2244  CAC CTT ACC CGC TCA CTT CGG CGT GCG GAG ACA GAG ACC AAA GTG CTC CAG GAG GCC CTG GCA GGC
       H   L   T   R   S   L   R   R   A   E   T   E   T   K   V   L   Q   E   A   L   A   G>

2310  CAG CTG GAC TCC AAC TGC CAG CCT ATG GCC ACC AAT TGG ATC CAG GAG AAA GTG TGG CTC TCT CAG
       Q   L   D   S   N   C   Q   P   M   A   T   N   W   I   Q   E   K   V   W   L   S   Q>

2376  GAG GTG GAC AAA CTG AGA GTG ATG TTC CTG GAG ATG AAA AAT GAG AAG GAA AAA CTC ATG ATC AAG
       E   V   D   K   L   R   V   M   F   L   E   M   K   N   E   K   E   K   L   M   I   K>

2442  TTC CAG AGC CAT AGA AAT ATC CTA GAG GAG AAC CTT CGG CGC TCT GAC AAG GAG TTA GAA AAA CTA
       F   Q   S   H   R   N   I   L   E   E   N   L   R   R   S   D   K   E   L   E   K   L>
```

(Boxed region at positions 1320–1386: "K H M Q A E L Q Q Q Q A V L A K E V R" — *leucine zipper motif*)

FIGURE 2 a

```
      GAT GAC ATT GTT CAG CAT ATT TAT AAG ACC CTG CTC TCT ATT CCA GAG GTG GTG AGG GGA TGC AGA
2508
       D   D   I   V   Q   H   I   Y   K   T   L   L   S   I   P   E   V   V   R   G   C   R>

GAA CTA CAG GGA TTG CTG GAA TTT CTG AGC TAA GAAACTGAAAGCCAGAATCTGCTTCACCTCTTTTTACCTGCA
2519
       E   L   Q   G   L   L   E   F   L   S   *>

ATACCCCCTTACCCCAATACCAAGACCAACTGGCATAGAGCCAACTGAGATAAATGCTATTTAAATAAAGTGTATTTAATGAAAAC
TCGTGCCGAATTCGGCACGAGCGGCACGAGCGGCACGAGCTGCAGCCATGTCTCTAGTGATCCCTGAAAAGTTCCAGCATATTTTGCG
AGTACTCAACACCAACATCGATGGGCGGCGGAAAATAGCCTTTGCCATCACTGCCATTAAGGGTGTGGGCCGAAGATATGCTCATGT
GGTGTTGAGGAAAGCAGACATTGACCTCACCAAGAGGGCGGGAGAACTCACTGAGGATGAGGTGGAACGTGTGATCACCATTATGCA
GAATCCACGCCAGTACAAGATCCCAGACTGGTTCTTGAACAGACAGAAGGATGTAAAGGATGGAAAATACAGCCAGGTCCTAGCCAAT
GGTCTGGACAACAAGCTCCGTGAAGACCTGGAGCGACTGAAGAAGATTCGGGCCCATAGAGGGCTGCGTCACTTCTGGGGCCTTCGTG
TCCGAGGCCAGCACACCAAGACCACTGGCCGCCGTGGCCGCACCGTGGGTGTGTCCAAGAAGAAATAAGTCTGTAGGCCTTGTCTGTT
AATAAATAGTTTATATACCAAAAAAAAAAAAAAAAAAACTCGAGCATGCATCTAGAGGGCCC
```

FIGURE 2 b

Sequence of 091-132Q20   Calculated Molecular Weight = 45904.93   Estimated pI = 6.73

```
  66  GAA CTA GTG GAT CCC CCG GGC TGC AGG AAT TCG GCA CGA GGC GGC GCC GAA GAG GCG ACT GAG GCC
       E   L   V   D   P   P   G   C   R   N   S   A   R   G   G   A   E   E   A   T   E   A>

132  GGA CGG GGC GGA CGG CGA CGC AGC CCG CGG CAG AAG TTT GAA ATT GGC ACA ATG GAA GAA GCT GGA
       G   R   G   G   R   R   R   S   P   R   Q   K   F   E   I   G   T   M   E   E   A   G>

198  ATT TGT GGG CTA GGG GTG AAA GCA GAT ATG TTG TGT AAC TCT CAA TCA AAT GAT ATT CTT CAA CAT
       I   C   G   L   G   V   K   A   D   M   L   C   N   S   Q   S   N   D   I   L   Q   H>

264  CAA GGC TCA AAT TGT GGT GGC ACA AGT AAC AAG CAT TCA TTG GAA GAG GAT GAA GGC AGT GAC TTT
       Q   G   S   N   C   G   G   T   S   N   K   H   S   L   E   E   D   E   G   S   D   F>

330  ATA ACA GAG AAC AGG AAT TTG GTG AGC CCA GCA TAC TGC ACG CAA GAA TCA AGA GAG GAA ATC CCT
       I   T   E   N   R   N   L   V   S   P   A   Y   C   T   Q   E   S   R   E   E   I   P>

396  GGG GGA GAA GCT CGA ACA GAT CCC CCT GAT GGT CAG CAA GAT TCA GAG TGC AAC AGG AAC AAA GAA
       G   G   E   A   R   T   D   P   P   D   G   Q   Q   D   S   E   C   N   R   N   K   E>

462  AAA ACT TTA GGA AAA GAA GTT TTA TTA CTG ATG CAA GCC CTA AAC ACC CTT TCA ACC CCA GAG GAG
       K   T   L   G   K   E   V   L   L   L   M   Q   A   L   N   T   L   S   T   P   E   E>
                         └─────────────── leucine zipper ───────────────┘

528  AAG CTG GCA GCT CTC TGT AAG AAA TAT GCT GAT CTT CTG GAG GAG AGC AGG AGT GTT CAG AAG CAA
       K   L   A   A   L   C   K   K   Y   A   D   L   L   E   E   S   R   S   V   Q   K   Q>

594  ATG AAG ATC CTG CAG AAG AAG CAA GCC CAG ATT GTG AAA GAG AAA GTT CAC TTG CAG AGT GAA CAT
       M   K   I   L   Q   K   K   Q   A   Q   I   V   K   E   K   V   H   L   Q   S   E   H>

660  AGC AAG GCT ATC TTG GCA AGA AGC AAG CTA GAA TCT CTT TGC AGA GAA CTT CAG CGT CAC AAT AAG
       S   K   A   I   L   A   R   S   K   L   E   S   L   C   R   E   L   Q   R   H   N   K>

726  ACG TTA AAG GAG GAA AAT ATG CAG CAG GCA CGA GAG GAA GAA GAA CGA CGT ATA GAA GCA ACT GCA
       T   L   K   E   E   N   M   Q   Q   A   R   E   E   E   E   R   R   I   E   A   T   A>

792  CAT TTC CAG ATT ACC TTA AAT GAA ATT CAA GCC CAG CTG GAG CAG CAT GAC ATC CAC AAC GCC AAA
       H   F   Q   I   T   L   N   E   I   Q   A   Q   L   E   Q   H   D   I   H   N   A   K>

858  CTC CGA CAG GAA AAC ATT GAG CTG GGG GAG AAG CTA AAG AAG CTC ATC GAA CAG TAC GCA CTG AGG
       L   R   Q   E   N   I   E   L   G   E   K   L   K   K   L   I   E   Q   Y   A   L   R>

924  GAA GAG CAC ATT GAT AAG GTG TTC AAA CAT AAG GAA CTG CAA CAG CAG CTC GTG GAT GCC AAA CTG
       E   E   H   I   D   K   V   F   K   H   K   E   L   Q   Q   Q   L   V   D   A   K   L>

990  CAG CAA ACG ACA CAA CTG ATA AAA GAA GCT GAT GAA AAA CAT CAG AGA GAG AGA GAG TTT TTA TTA
       Q   Q   T   T   Q   L   I   K   E   A   D   E   K   H   Q   R   E   R   E   F   L   L>

1056  AAA GAA GCG ACA GAA TCG AGG CAC AAA TAC GAA CAA ATG AAA CAG CAA GAA GTA CAA CTA AAA CAG
       K   E   A   T   E   S   R   H   K   Y   E   Q   M   K   Q   Q   E   V   Q   L   K   Q>

1122  CAG CTT TCT CTT TAT ATG GAT AAG TTT GAA GAA TTC CAG ACT ACC ATG GCA AAA AGC AAT GAA CTG
       Q   L   S   L   Y   M   D   K   F   E   E   F   Q   T   T   M   A   K   S   N   E   L>

1191  TTT ACA ACC TTC AGA CAG GAA ATG GAA AAG ATG ACA AAG AAA ATT AAA AAA AAA AAA AAA CTC GAG
       F   T   T   F   R   Q   E   M   E   K   M   T   K   K   I   K   K   K   K   K   L   E>
```

FIGURE 3

MODULATORS OF BRCA1 ACTIVITY

FIELD OF THE INVENTION

The invention described herein relates generally to the field of human disease, and more specifically to treating and diagnosing disease based on the presence of modulators of BRCA1 activity.

BACKGROUND

Breast cancer is one of the leading causes of cancer deaths of women in the United States, and approximately 170,000 women are affected by the disease each year. About 5% of these reported cases are thought to result from a patient's genetic predisposition to the disease. Breast cancer is generally considered to be classifiable as early-age onset and late-age onset, the latter being defined as occurring at about age 50. Approximately 25% of patients diagnosed with breast cancer before the age of 40 are thought to be familial, and thus have an underlying genetic component. Late-age onset breast cancer is also often familial although the risks of a family member developing the disease is less compared to early-age onset if relatives have presented with the disease.

As a result of studies involving families with inherited early onset breast and ovarian cancers a gene thought to be involved in these diseases has been mapped to the long arm of chromosome 17 and termed BRCA1, or breast cancer one gene. See, Hitoyuki, T., et al., Cancer res. vol. 55: 2998–3002. Additional studies on sporadic cases of breast cancer have also established a genetic link with this disease to BRCA1 which was more precisely localized to the chromosomal region 17q21. See, Hall, J. M., et al. Science, vol. 250: 1684–1689 (1990).

Recently, the BRCA1 gene has been cloned, and shown to encode a protein having the properties of a tumor suppressor protein. See, Miki, Y., et al Science, vol. 266: 66–71; and WO96/05306. It has been known for some time that a variety of cancers are caused, at least in part, by mutations to certain normal genes, termed "proto-oncogenes." Proto-oncogenes are involved in regulating normal cell growth in ways that are only now beginning to be appreciated at the molecular level. The mutated proto-oncogenes, or cancer causing genes termed "oncogenes," disrupt normal cell growth which ultimately causes the death of the organism, if the cancer is not detected and treated in time. During normal or cancer cell growth, proto-oncogenes or oncogenes, are counterbalanced by growth-regulating proteins which regulate or try to regulate the growth of normal or cancer cells, respectively. Such proteins are termed "tumor suppressor proteins," and include BRCA1, p53, retinoblastoma protein (Rb), adenomatous polyposis coli protein (APC), Wilm's tumor 1 protein (WT1), neurofibromatosis type 1 protein (NF1), and neurofibromatosis type 2 protein (NF2).

BRCA1 cDNA encodes a 1863 amino acid protein with a predicted molecular weight of approximately 207,000. See, Miki, Y., et al. (1994) Science vol. 266, pages 66–71. The cloning and characterization of BRCA1 has facilitated establishing it as a tumor suppressor protein. For example, recent work by several investigators have shown that transfection and expression of the BRCA1 gene sequence into MCF-7 tumor cells retards tumor growth in vivo and extends the survival time of tumor bearing animals. See, Holt, J. T., et al, (1996) Nat. Genet. vol. 12, pages 298–302. Similar results were obtained using a retroviral vector expressing wild-type BRCA1 against an established MCF-7 peritoneal tumor.

Considerable work has been done to identify those regions of BRCA1 that affects its tumor suppressor activity. It appears that different regions of the molecule may affect its tumor suppressor activity differently. For instance, near full length truncated BRCA1 proteins do not inhibit breast cancer cell growth, but do inhibit ovarian cancer cell growth. See, Holt, J. T., et al, (1996) Nat. Genet. vol. 12, pages 298–302. These observations strongly suggest that different host cell factors, presumably proteins, are interacting with different regions of BRCA1 to affect cell growth.

Over the past several years, the interactions of certain tumor suppressor proteins with host cell proteins have begun to be elucidated. See, Levin, A., Annu. Rev. Biochem. 1993, vol. 62: pages 623–651. The identification of proteins involved in these interactions will facilitate the development of novel diagnostic methods, as well as novel therapeutics for identifying and treating cancer. For example, the retinoblastoma tumor suppressor protein is phosphorylated at serine residues adjacent to a proline. The level of phosphorylation is high through S, G2, and M-phase of the cell cycle. The kinase that effects this reaction is, in turn, activated by a cyclin that regulates events in the cell cycle. Subsequently, in late mitosis, a phosphatase removes the phosphate groups from the protein, and returns the retinoblastoma tumor suppressor protein to an unphosphorylated state in Go-G1. Clearly, the identification of drugs that can effect these interactions can be expected to play a critical role in regulating cell growth and thus be useful in the treatment of cancer.

To date, however, there have been few, if any studies on the interaction of proteins with the tumor suppressor protein, BRCA1. In order to better develop methods to diagnosis and treat both breast and ovarian cancer the identification and isolation of such proteins is critical.

SUMMARY OF THE INVENTION

A first object of the invention is to describe a family of related isolated nucleic acid sequences that encode proteins, hereinafter referred to as Modulator Proteins, that bind to the tumor suppressor protein BRCA1.

A second object of the invention is to describe a family of related isolated nucleic acid sequences that encode BRCA1 Modulator Proteins having a range of molecular weights ranging from about 45–97 kdaltons, at least one leucine zipper domain, and optionally a zinc finger domain, that bind BRCA1 at a discreet sequence for Modulator Protein binding that is encompassed in the first six hundred amino acids of BRCA1.

A third object of the invention is to describe a BRCA1 Modulator Protein having a calculated molecular weight of about 53 kdaltons that has one leucine zipper domain and a zinc finger domain, both domains near the amino terminal region of the molecule, that bind BRCA1 at a consenus sequence for Modulator Protein binding encompassed within the first six hundred amino acids of BRCA1.

A fourth object of the invention is to describe isolated nucleic acid or protein fragments of BRCA1 Modulator Protein (s), respectively.

A fifth object of the invention is to describe host cells transformed with isolated nucleic acid sequences that encodes BRCA1 Modulator Protein(s) or fragments thereof.

A sixth object of the invention is to describe vectors that contain isolated nucleic acid sequences that encode BRCA1 Modulator Protein(s) or fragments thereof.

A seventh object of the invention is to describe complexes consisting of full length or fragments of BRCA1 and BRCA1 Modulator Proteins.

An eighth object of the invention is to describe methods of diagnosing disease, preferably those involving unwanted cell growth, including cancer, using isolated nucleic acid sequences, or fragments thereof, that encode a BRCA1 Modulator Protein, or fragments thereof.

A ninth object of the invention is to describe an assay for identifying compounds that would have therapeutic applications for the treatment of diseases involving unwanted cell growth, including cancer.

These and other objects of the present invention will become apparent to one of ordinary skill in the art upon reading the description of the various aspects of the invention in the following specification. The foregoing and other aspects of the present invention are explained in greater detail in the drawings, detailed description, and examples set forth below.

BRIEF DESCRIPTION OF THE DRAWINGS

FIG. 1 shows the cDNA and amino acid sequence of the BRCA1 Modulator Protein, depicted in Sequence ID No. 1, 091-21A31.

FIG. 2 shows the cDNA and amino acid sequence of the BRCA1 Modulator Protein, depicted in Sequence ID No. 3, 091-1F84.

FIG. 3 shows the cDNA and amino acid sequence of the BRCA1 Modulator Protein, depicted in Sequence ID No. 5, 091-132Q20.

Figure 4:
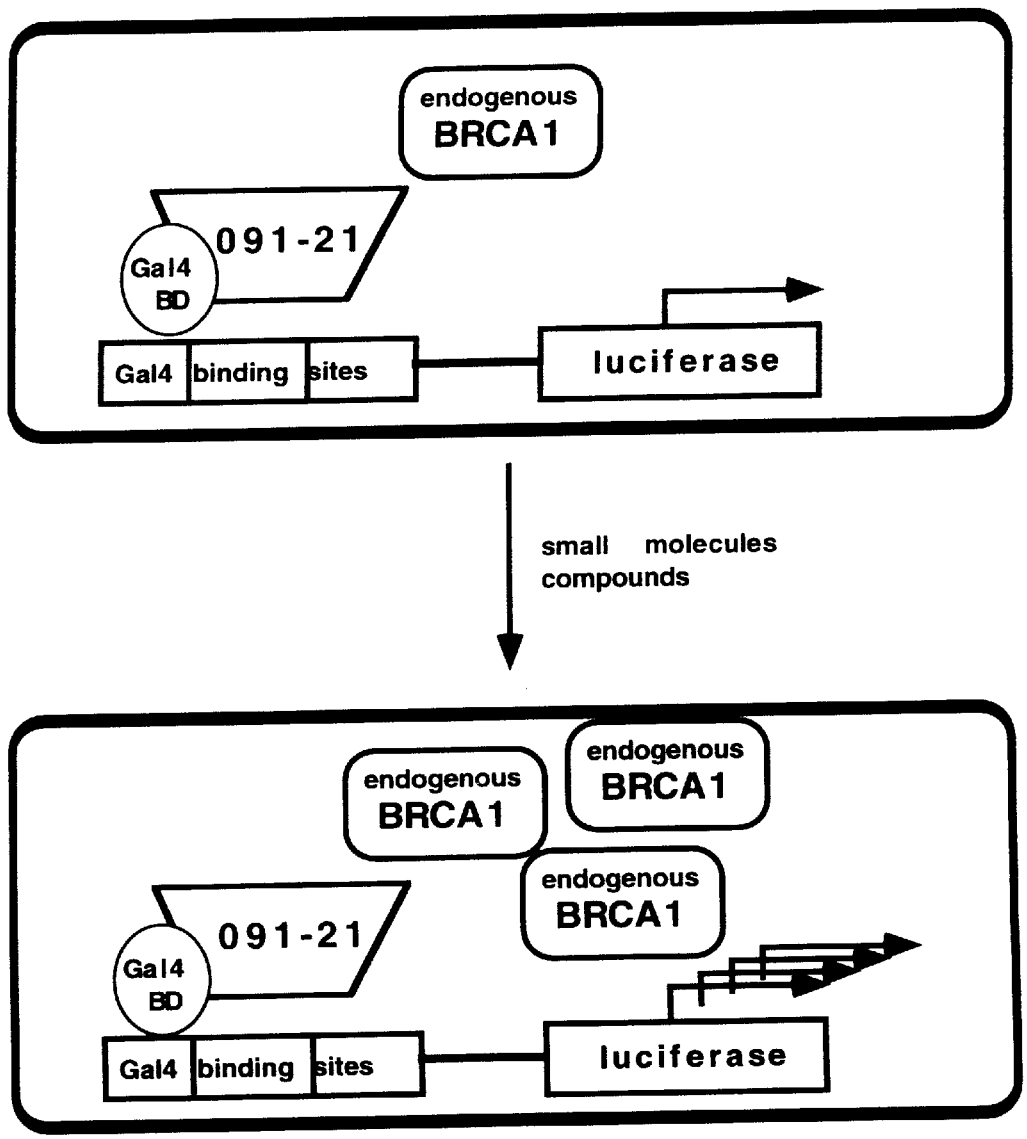
FIG. 4 shows the format of an assay to identify compounds that increase the intracellular levels of BRCA1.

Table 1 shows the regions of BRCA1 that interact with the BRCA1 Modulator Proteins 091-1F84, Sequence ID No. 3, 091-21A31, Sequence ID No. 1 and 091-132Q20, Sequence ID No. 5. The experiment was conducted using the two-hybrid assay as described in U.S. Pat. No. 5,283,173, or Chien et al., 1991, Proc. Natl. Acad. Sci. USA, 88: 9578–9582. The cDNAs that encode 091-1F84, Sequence ID No. 3, 091-21A31, Sequence ID No. 1 and 091-132Q20, Sequence ID No. 5 were fused to the GAL 4 activation domain, and those regions of BRCA1 shown in the table were fused to the binding domain of GAL4. The "+" sign is a subjective measure of the amount of b-galactosidase activity. One "+" being the lowest, and three "+++" being the highest activity.

Table 2 shows regions of the BRCA1 Modulator Protein 091-21A31, Sequence ID No. 1 that interact with regions of BRCA1.

DETAILED DESCRIPTION OF THE INVENTION

All publications and patent applications mentioned in this specification are herein incorporated by reference to the same extent as if each individual publication or patent application was specifically and individually indicated to be incorporated by reference.

Definitions

At the outset it is worth noting that unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see generally, Sambrook et al., *Molecular Cloning: A Laboratory Manual*, 2nd. edition (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

In the formulas representing selected specific embodiments of BRCA1 or BRCA1 Modulator Proteins of the present invention, the amino- and carboxy-terminal groups, although often not specifically shown, will be understood to be in the form they would assume at physiological pH values, unless otherwise-specified. Thus, the N-terminal $H_2^+$ and C-terminal-$O^-$ at physiological pH are understood to be present though not necessarily specified and shown, either in specific examples or in generic formulas. In the polypeptide notation used herein, the left-hand end of the molecule is the amino terminal end and the right-hand end is the carboxy-terminal end, in accordance with standard usage and convention. Of course, the basic and acid addition salts including those which are formed at nonphysiological pH values are also included in the compounds of the invention. The amino acid residues described herein are preferably in the "L" isomeric form. Stereoisomers (e.g., D-amino acids) of the twenty conventional amino acids, unnatural amino acids such as a,a-distributed amino acids, N-alkyl amino acids, lactic acid, and other unconventional amino acids may also be suitable components for polypeptides of the present invention, as long as the desired functional property is retained by the polypeptide. For the peptides shown, each encoded residue where appropriate is represented by a three letter designation, corresponding to the trivial name of the conventional amino acid, in keeping with standard polypeptide nomenclature (described in *J. Biol. Chem.*, 243: 3552–59 (1969) and adopted at 37 CFR §1.822(b)(2)).

Free functional groups, including those at the carboxy- or amino-terminus, referred to as noninterfering substituents, can also be modified by amidation, acylation or other substitution, which can, for example, change the solubility of the compounds without affecting their activity. This may be particularly useful in those instances where BRCA1 Modulator Proteins are known to have certain regions that bind to BRCA1, and it is desirable to make soluble peptides from these regions.

As employed throughout the disclosure, the following terms, unless otherwise indicated, shall be understood to have the following meanings:

The term "isolated protein" referred to herein means a protein of cDNA, recombinant RNA, or synthetic origin or some combination thereof, which by virtue of its origin the "isolated protein" (1) is not substantially associated with proteins found in nature, (2) is substantially free of other proteins from the same source, e.g. free of human proteins, (3) may be expressed by a cell from a different species, or (4) does not occur in nature.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides. The term "naturally occurring nuclnucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoroaniladate, phosphoroamidate, and the like. An oligonucleotide can include a label for detection, if desired.

The term "sequence homology" referred to herein describes the proportion of base matches between two nucleic acid sequences or the proportion amino acid matches between two amino acid sequences. When sequence homology is expressed as a percentage, e.g., 50%, the percentage denotes the proportion of matches over the length of sequence from BRCA1 that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and most preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M.O., in Atlas of Protein Sequence and Structure, 1972, volume 5, National Biomedical Research Foundation, pp. 101–110, and Supplement 2 to this volume, pp. 1–10. The two sequences or parts thereof are more preferably homologous if their amino acids are greater than or equal to 50% identical when optimally aligned using the ALIGN program.

One of the properties of a BRCA1 Modulator Protein is the presence of a leucine zipper domain. The latter is defined as a stretch of amino acids rich in leucine residues, generally every seventh residue, which provide a means whereby a protein may dimerize to form either homodimers or heterodimers. Examples of proteins with leucine zippers include Jun and Fos.

An optional property of a BRCA1 Modulator Protein is the presence of a zinc finger domain, preferably of the type $C_3H_2C_3$, $C_3HC_4$, or $CX_2CX_{11-27}CXHX_2H$ or $CX_2CX_{6-17}CX_2C$; where C, X, and H denote cysteine, an amino acid, and histidine, respectively. The domain binds zinc ions, and is often associated with proteins that bind DNA. Such domains are readily identified using an appropriate data base known to a skilled practitioner of this art, particularly the Prosite Protein Database.

As used herein, "substantially pure" means an object species is the predominant species present (i.e., on a molar basis it is more abundant than any other macromolecular individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The phrases "Modulator Protein," "Modulator Peptide," or "Modulator Polypeptide" refer to proteins or peptides that affect the activity of the BRCA1 gene or the protein encoded by the gene. Each of these definitions is meant to encompass one or more such entities.

Chemistry terms herein are used according to conventional usage in the art, as exemplified by The McGraw-Hill Dictionary of Chemical Terms (ed. Parker, S., 1985), McGraw-Hill, San Francisco, incorporated herein by reference.

The production of proteins from cloned genes by genetic engineering is well known. See, e.g. U.S. Pat. No. 4,761,371 to Bell et al. at column 6, line 3 to column 9, line 65. (The disclosure of all patent references cited herein is to be incorporated herein by reference.) The discussion which follows is accordingly intended as an overview of this field, and is not intended to reflect the full state of the art.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading frame.

Suitable host cells include prokaryotes, yeast cells, or higher eukaryotic cells. Prokaryotes include gram negative or gram positive organisms, for example *Escherichia coli* (*E. coli*) or Bacilli. Higher eukaryotic cells include established cell lines of mammalian origin as described below. Exemplary host cells are DH5a, *E. coli* W3110 (ATCC 27,325), *E coli* B, *E. coli* X1776 (ATCC 31,537) and *E. coli*

294 (ATCC 31,446). Pseudomonas species, Bacillus species, and Serratia marcesans are also suitable.

In an insect system, *Autographa californica* nuclear polyhidrosis virus (AcNPV) may be used as a vector to express foreign genes. (E.g., see Smith et al., 1983, J. Virol. 46: 584; Smith, U.S. Pat. No. 4,215,051). In a specific embodiment described below, Sf9 insect cells are infected with a baculovirus vector expressing a glu-glu epitope tagged BRCA1 Modulator construct. See, Rubinfeld, et al., J. Biol. Chem. vol. 270, no. 10, pp 5549–5555 (1995). Other epitope tags may be employed that are known in the art including a 6x histidine tag, myc, or an EE-tag (i.e. Glu-Glu-tag). "E" refers to the amino acid glutamine.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., Gene 2, 95 (1977). pBR322 contains genes for ampicillin and tetracycline resistance and thus provides easy means for identifying transformed cells. Expression vectors should contain a promoter which is recognized by the host organism. This generally means a promoter obtained from the intended host. Promoters most commonly used in recombinant microbial expression vectors include the betalactamase (penicillinase) and lactose promoter systems (Chang et al., Nature 275, 615 (1978); and Goeddel et al., Nucleic Acids Res. 8, 4057 (1980) and EPO Application Publication Number 36,776) and the tac promoter (H. De Boer et al., Proc. Natl. Acad. Sci. USA 80, 21 (1983)). While these are commonly used, other microbial promoters are suitable. Details concerning nucleotide sequences of many promoters have been published, enabling a skilled worker to operably ligate them to DNA encoding BRCA1 in plasmid or viral vectors (Siebenlist et al., Cell 20, 269, 1980)). The promoter and Shine-Dalgarno (SD) sequence (for prokaryotic host expression) are operably linked to the DNA encoding BRCA1, i.e. they are positioned so as to promote transcription of the BRCA1 messenger RNA from the DNA. The SD sequence is thought to promote binding of mRNA to the ribosome by the pairing of bases between the SD sequence and the 3' end of *E. coli* 16S rRNA (Steitz et al. (1979). In *Biological Regulation and Development: Gene Expression* (ed. R. F. Goldberger)). To express eukaryotic genes and prokaryotic genes with a weak ribosome-binding site see Sambrook et al. (1989) "Expression of cloned genes in *Escherichia coli*." In *Molecular Cloning: A Laboratory Manual*. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) *J. Mol. Biol.* 189: 113; Tabor et al. (1985) *Proc. Natl. Acad. Sci.* 82: 1074). In addition, a hybrid promoter can also be composed of a bacteriophage promoter and an *E. coli* operator region (EPO Pub. No. 267,851).

BRCA1 Modulators can be expressed intracellularly. A promoter sequence can be directly linked with a BRCA1 Modulator gene or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase (EPO Pub. No. 219,237).

Eukaryotic microbes such as yeast cultures may be transformed with suitable BRCA1 Modulator vectors. See, e.g. U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding BRCA1 Modulator, sequences for polyadenylation and transcription termination, and a selection gene.

Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., J. Adv. Enzyme Reg. 7, 149 (1968); and Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promotes for use in yeast expression are further described in R. Hitzman et al., EPO Publication Number 73,657.

Cultures of cells derived from multicellular organisms are a desirable host for recombinant BRCA1 Modulator synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See Tissue Culture, Academic Press, Kruse and Paterson, editors (1973).

The transcriptional and translational control sequences in expression vectors to be used in transforming vertebrate cells are often provided by viral sources. For example, commonly used promoters are derived from CMV, polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Identification of BRCA1 Modulators

BRCA1 Modulators can be identified using several different techniques for detecting protein-protein interactions. Among the traditional methods which may be employed are co-immunoprecipitation, crosslinking and co-purification through gradients or chromatographic columns of cell lysates, or proteins obtained from cell lysates using BRCA1 to identify proteins in the lysate that interact with BRCA1. Such assays may employ full length BRCA1 or a BRCA1 peptide. Once isolated, such an intracellular protein can be identified and can, in turn, be used, in conjunction with standard techniques, to identify proteins with which it interacts. For example, at least a portion of the amino acid sequence of an intracellular protein which interacts with BRCA1, can be ascertained using techniques well known to those of skill in the art, such as the Edman degradation technique. (See, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra., and PR Protocols: A Guide to Methods and Applications, 1990, Innis, M. et al., eds. Academic Press, Inc., New York).

Additionally, methods may be employed which result in the simultaneous identification of genes which encode the intracellular proteins interacting with BRCA1. These methods include, for example, probing expression libraries, in a manner similar to the well known technique of antibody probing of λgt11 libraries, using labeled BRCA1 protein, or fusion protein, e.g., BRCA1 fused to a marker (e.g., an enzyme, fluor, luminescent protein, or dye), or an Ig-Fc domain.

One method which detects protein interactions in vivo, the two-hybrid system is described in detail for illustration only and not by way of limitation. This system has been described ( U.S. Pat. No. 5,283,173 Chien et al., 1991, Proc. Natl. Acad. Sci. USA, 88: 9578–9582) and is commercially available from Clontech (Palo Alto, Calif.). Briefly, utilizing such a system, plasmids are constructed that encode two hybrid proteins: one plasmid consists of nucleotides encoding the DNA-binding domain of a transcription activator protein fused to a BRCA1 nucleotide sequence encoding BRCA1, or BRCA1 peptide or fusion protein, and the other plasmid consists of nucleotides encoding the transcription activator protein's activation domain fused to a cDNA encoding an unknown protein which has been recombined into this plasmid as a part of the cDNA library. The DNA-binding domain fusion plasmid and the cDNA library are transformed into a strain of the yeast *Saccharomyces cerevisiae* that contains a reporter gene (e.g., HIS3 or lacZ) whose regulatory region contain the transcription activator's binding site. Either hybrid protein alone cannot activate transcription of the reporter gene; the DNA-binding domain hybrid cannot because it does not provide activation function, and the activation domain hybrid cannot because it cannot localize to the activator's binding sites. Interaction of the two hybrid proteins reconstitutes the functional activator protein and results in transcriptional activation of the reporter gene, which is detected by an assay for the reporter gene product.

The two-hybrid system or related methodology may be used to screen activation domain libraries for proteins that interact with the "bait" gene product. By way of example, and not by way of limitation, preferrably BRCA1 peptides, or fusion proteins are used as the bait gene product. Full length BRCA1 alone can act as a transcriptional activator protein and thus cannot serve as "bait." Total genomic or cDNA sequences are fused to the DNA encoding an activation domain. This library and a plasmid encoding a hybrid of a bait BRCA1 gene product fused to the DNA-binding domain are cotransformed into a yeast reporter strain, and the resulting tranformants are screened for those that have transcriptionally activated reporter gene. For example, and not by way of limitation, a bait BRCA1 gene sequence, such as the open reading frame of BRCA1 (or a domain of BRCA1) can be cloned into a vector such that it is translationally fused to the DNA encoding the DNA-binding domain of the GAL4 protein. These colonies are purified and the library plasmids responsible for reporter gene transcription are isolated. DNA sequencing is then used to determine the nucleotide sequence of the clones which, in turn, reveals the identity of the protein sequences encoded by the library plasmids.

A cDNA library of the cell line from which proteins that interact with bait BRCA1 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait BRCA1 gene-GAL4 fusion plasmid into a yeast strain which contains a lacZ gene driven by a promoter which contains GAL4 activation sequence. A cDNA encoded protein, fused to GAL4 transcriptional activation domain, that interacts with bait BRCA1 gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait BRCA1 gene-interacting protein using techniques routinely practiced in the art.

Using the above described two-hybrid technique several BRCA1 modulators were identified, and shown to share certain properties including a leucine zipper domain.

BRCA1 Modulator cDNA

The cDNA, and deduced amino acid sequences, of three representative BRCA1 Modulator Proteins are shown in FIGS. 1–3. The cDNAs or the proteins that they encode are hereinafter referred to as 091-21A31, Sequence ID No. 1, 091-1F84, Sequence ID No. 3, and 091-132Q20, Sequence ID No. 5. The cDNAs encode proteins that have calculated molecular weights in the range of about 45–97 kd. Particularly noteworthy is the presence of at least one leucine zipper motif, and optionally a zinc finger domain.

The BRCA1 Modulator Protein nucleotide sequences of the invention include: (a)the DNA sequences shown in FIGS. 1–3 or contained in the cDNA clones as deposited with the American Type Culture Collection on Aug. 14, 1996 (ATCC) under accession numbers 98141 (091-1F84, Sequence ID No. 3), 98142 (091-21A31, Sequence ID No. 1), and 98143 (091-132Q20, Sequence ID No. 5); (b) and any nucleotide sequence that hybridizes to the complement of the DNA sequence shown in FIGS. 1–3 or contained in the cDNA clones as deposited with the ATCC under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F.M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and (c) any nucleotide sequence that hybridizes to the complement of the DNA sequences that encode the amino acid sequence shown in FIGS. 1–3 or contained in the cDNA clones as deposited with the ATCC, as described above, under less stringent conditions, such as moderately stringent conditions, e.g., washing in 0.2×SSC/0.1% SDS at 42° C. (Ausubel et al., 1989, supra), yet which still encodes a functionally equivalent BRCA1 Modulator Protein gene product. Functional equivalents include naturally occurring BRCA1 Modulator Protein genes present in other species, and mutant BRCA1 Modulator Protein genes whether naturally occurring or engineered which retain at least some of the functional activities of a BRCA1 Modulator Protein (i.e., binding to BRCA1). The invention also includes degenerate variants of sequences (a) through (c).

The invention also includes nucleic acid molecules, preferably DNA molecules, that hybridize to, and are therefore the complements of, the nucleotide sequences (a)through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/ 0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as BRCA1 Modulator gene antisense molecules, useful, for example, in gene regulation (for and/or as antisense primers in amplification reactions of BRCA1 Modulator gene nucleic acid sequences). Such sequences may be used as part of ribozyme and/or triple helix sequences, also useful for BRCA1 Modulator gene regulation. Still further, such molecules may be used as components of diagnostic methods whereby, for example, the presence of a particular BRCA1 Modulator allele associated with uncontrolled cell growth (i.e. cancer) may be detected.

Further, it will be appreciated by one skilled in the art that a BRCA1 Modulator gene homolog may be isolated from nucleic acid of an organism of interest by performing PCR using two degenerate oligonucleotide primer pools designed on the basis of amino acid sequences within the BRCA1 Modulator gene product disclosed herein. The template for the reaction may be cDNA obtained by reverse transcription of mRNA prepared from, for example, human or non-human cell lines or cell types, such as breast or ovarian cells, known or suspected to express a BRCA1 Modulator gene allele.

The PCR product may be subcloned and sequenced to ensure that the amplified sequences represent the sequences of a BRCA1 Modulator gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular source (i.e., one known, or suspected, to express a BRCA1 Modulator gene, such as, for example, from breast or ovarian cells). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

A cDNA of a mutant BRCA1 Modulator gene may also be isolated, for example, by using PCR. In this case, the first cDNA strand may be synthesized by hybridizing an oligo-dT oligonucleotide to mRNA isolated from cells known or suspected to be expressed in an individual putatively carrying the mutant BRCA1 Modulator allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant BRCA1 Modulator allele to that of the normal BRCA1 Modulator allele, the mutation(s) responsible for the loss or alteration of function of the mutant BRCA1 Modulator gene product can be ascertained.

A genomic library can be constructed using DNA obtained from an individual suspected of or known to carry the mutant BRCA1 Modulator allele, or a cDNA library can be constructed using RNA from a cell type known, or suspected, to express the mutant BRCA1 Modulator allele. The normal BRCA1 Modulator gene or any suitable fragment thereof may then be labeled and used as a probe to identify the corresponding mutant BRCA1 Modulator allele in such libraries. Clones containing the mutant BRCA1 Modulator gene sequences may then be purified and subjected to sequence analysis according to methods well known to those of skill in the art.

Additionally, an expression library can be constructed utilizing cDNA synthesized from, for example, RNA isolated from a cell type known, or suspected, to express a mutant BRCA1 Modulator allele in an individual suspected of or known to carry such a mutant allele. In this manner, gene products made by the putatively mutant cell type may be expressed and screened using standard antibody screening techniques in conjunction with antibodies raised against the normal BRCA1 Modulator gene product, as described, below. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled fusion proteins. In cases where a BRCA1 Modulator mutation results in an expressed gene product with altered function (e.g., as a result of a missense or a frameshift mutation), a polyclonal set of antibodies to a BRCA1 Modulator are likely to cross-react with the BRCA1 Modulator mutant. Such BRCA1 Modulator mutants detected via their reaction with labeled antibodies can be purified and subjected to sequence analysis according to methods well known to those of skill in the art.

The invention also encompasses nucleotide sequences that encode peptide fragments of a BRCA1 Modulator, truncated BRCA1 Modulators, and fusion proteins of a BRCA1 Modulator. Nucleotides encoding fusion proteins may include but are not limited to full length BRCA1 Modulators, truncated BRCA1 Modulators or peptide fragments to an unrelated protein or peptide, such as for example, an epitope tag which aids in purification or detection of the resulting fusion protein; or an enzyme, fluorescent protein, luminescent protein which can be used as a marker. The preferred epitope tag is glu-glu as described by Rubinfeld, B., et al., J. Biol. Chem. vol. 270, no. 10, pp 5549–5555 (1995), and Grussenmyer, T., et al., Proc. Natl. Acad. Sci. U.S.A. vol. 82, pp. 7952–7954 (1985).

The invention also encompasses (a) DNA vectors that contain any of the foregoing BRCA1 Modulator coding sequences and/or their complements (i.e., antisense); (b) DNA expression vectors that contain any of the foregoing BRCA1 Modulator coding sequences operatively associated with a regulatory element that directs the expression of the coding sequences; and (c) genetically engineered host cells that contain any of the foregoing BRCA1 Modulator coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the baculovirus promoter, cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast-mating factors.

BRCA1 Modulator Proteins

As mentioned above, FIGS. 1–3 shows the cDNA, and deduced amino acid sequences, of three representative BRCA1 Modulator Proteins; 091-21A31, Sequence ID No. 1, 091-1F84, Sequence ID No. 3, and 091-132Q20, Sequence ID No. 5. 091-132Q20, Sequence ID No. 5 is not a full length sequence. The proteins have calculated molecular weights in the range of about 45–97 kd. Particularly noteworthy is the presence of at least one leucine zipper motif, and optionally a zinc finger domain. For instance, 091-1F84, Sequence ID No. 3 has two leucine zippers, 091-132Q20, Sequence ID No. 5 has a single leucine zipper, while 091-21A31, Sequence ID No. 1 has a single leucine zipper and a zinc finger domain. Such domains are readily identified using the Prosite Protein Database.

The invention BRCA1 Modular Proteins, peptide fragments, mutated, truncated or deleted forms of and fusion proteins of these can be prepared for a variety of uses, including but not limited to the generation of antibodies, as reagents in diagnostic assays, the identification and/or the interaction with other cellular gene products involved in cell growth, as reagents in assays for screening for compounds that can be used in the treatment of unwanted cell growth disorders, including but not limited to cancer, and as pharmaceutical reagents useful in the treatment of such diseases.

By way of example, the 091-21A31, Sequence ID No. 1 BRCA1 Modulator Protein sequence begins with a methionine in a DNA sequence context consistent with a translation initiation site. The predicted molecular mass of this BRCA1 Modulator Protein is 53.3 kD.

The BRCA1 Modulator Protein amino acid sequences of the invention include the amino acid sequence shown in FIG. 1, or the amino acid sequence encoded by the cDNA clone, as deposited with the ATCC, as described above. Further, BRCA1 Modulator Proteins of other species are encompassed by the invention. In fact, any BRCA1 Modulator Protein protein encoded by the cDNAs described above, are within the scope of the invention.

The invention also encompasses proteins that are functionally equivalent to the BRCA1 Modulator Protein encoded by the nucleotide sequences described above, as judged by any of a number of criteria, including but not limited to the ability to bind BRCA1, the binding affinity for BRCA1, a change in cellular metabolism or change in phenotype when the BRCA1 Modulator Protein equivalent is present in an appropriate cell type (such as ovarian or breast cells). Such functionally equivalent BRCA1 Modulator Protein proteins include but are not limited to additions or substitutions of amino acid residues within the amino acid sequence encoded by the BRCA1 Modulator nucleotide sequences described, above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to BRCA1 Modulator DNA (using random mutagenesis techniques well known to those skilled in the art) and the resulting mutant BRCA1 Modulator Proteins tested for activity, site-directed mutations of the BRCA1 Modulator coding sequence can be engineered (using site-directed mutagenesis techniques well known to those skilled in the art) to generate mutant BRCA1 Modulator Proteins with increased function, altered binding affinity for BRCA1.

For example, mutant BRCA1 Modulator Proteins can be engineered so that regions of interspecies identity are maintained, whereas the variable residues are altered, e.g., by deletion or insertion of an amino acid residue(s) or by substitution of one or more different amino acid residues. Conservative alterations at the variable positions can be engineered in order to produce a mutant BRCA1 Modulator Protein that retains function. Non-conservative changes can be engineered at these variable positions to alter function. Alternatively, where alteration of function is desired, deletion or non-conservative alterations of the conserved regions can be engineered. One of skill in the art may easily test such mutant or deleted BRCA1 Modulator Proteins for these alterations in function using the teachings presented herein.

Other mutations to a BRCA1 Modulator coding sequence can be made to generate BRCA1 Modulator Proteins that are better suited for expression, scale up, etc. in the host cells chosen. For example, the triplet code for each amino acid can be modified to conform more closely to the preferential codon usage of the host cell's translational machinery.

Peptides corresponding to one or more domains (or a portion of a domain) of a BRCA1 Modulator Protein (e.g., leucine zippers, zinc fingers), truncated or deleted BRCA1 Modulator Proteins (e.g., BRCA1 Modulator Proteins in which portions of one or more of the above domains are deleted) as well as fusion proteins in which the full length of a BRCA1 Modulator Protein, a BRCA1 Modulator Protein peptide or truncated BRCA1 Modulator Protein is fused to an unrelated protein are also within the scope of the invention and can be designed on the basis of a BRCA1 Modulator nucleotide and BRCA1 Modulator Protein amino acid sequences disclosed in this Section and above. Such fusion proteins include but are not limited to fusions to an epitope tag (such as is exemplified herein); or fusions to an enzyme, fluorescent protein, or luminescent protein which provide a marker function.

While the BRCA1 Modulator Proteins and peptides can be chemically synthesized (e.g., see Creighton, 1983, Proteins: Structures and Molecular Principles, W. H. Freeman & Co., N.Y.), large polypeptides derived from the BRCA1 Modulator Protein and the full length BRCA1 Modulator Protein itself may advantageously be produced by recombinant DNA technology using techniques well known in the art for expressing nucleic acid containing BRCA1 Modulator gene sequences and/or coding sequences. Such methods can be used to construct expression vectors containing the BRCA1 Modulator nucleotide sequences described above and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding BRCA1 Modulator nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the BRCA1 Modulator nucleotide sequences of the invention. Where a BRCA1 Modulator Protein peptide or polypeptide is a soluble secreted derivative the peptide or polypeptide can be recovered from the culture medium. If the BRCA1 Modulator Protein peptide or polypeptide is not secreted, it may be isolated from the host cells. However, such engineered host cells themselves may be used in situations where it is important not only to retain the structural and functional characteristics of a BRCA1 Modulator Protein, but to assess biological activity, e.g., in drug screening assays.

The expression systems that may be used for purposes of the invention include but are not limited to microorganisms such as bacteria (e.g., E. coli B. subtilis) transformed with recombinant bacteriophage DNA, plasmid DNA or cosmid DNA expression vectors containing BRCA1 Modulator nucleotide sequences; yeast (e.g., Saccharomyces, Pichia) transformed with recombinant yeast expression vectors containing the BRCA1 Modulator nucleotide sequences; insect cell systems infected with recombinant virus expression vectors (e.g., baculovirus) containing the BRCA1 Modulator sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing BRCA1 Modulator nucleotide sequences; or mammalian cell systems (e.g., COS, CHO, BHK, 293, 3T3, U937) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the BRCA1 Modulator gene product being expressed. For example, when a large quantity of such a protein is to be produced, for the generation of pharmaceutical compositions of BRCA1 Modulator Protein or for raising antibodies to the BRCA1 Modulator Protein, for example, vectors which direct the expression of high levels of fusion protein products that are readily purified may be desirable. Such vectors include, but are not limited, to the E. coli expression vector pUR278 (Ruther et al., 1983, EMBO J. 2: 1791), in which the BRCA1 Modulator coding sequence may be ligated individually into the vector in frame with the lacZ coding region so that a fusion protein is produced; pIN vectors (Inouye & Inouye, 1985, Nucleic Acids Res. 13: 3101–3109; Van Heeke & Schuster, 1989, J. Biol. Chem. 264: 5503–5509); and the like. pGEX vectors may also be used to express foreign polypeptides as fusion proteins with glutathione S-transferase (GST). If the inserted sequence encodes a relatively small polypeptide (less than 25 kD), such fusion proteins are generally soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. Alternatively, if the resulting fusion protein is insoluble and forms inclusion bodies in the host cell, the inclusion bodies may be purified and the recombinant protein solubilized using techniques well known to one of skill in the art.

In an insect system, Autographa californica nuclear polyhidrosis virus (AcNPV) may be used as a vector to express foreign genes. (E.g., see Smith et al., 1983, J. Virol. 46: 584; Smith, U.S. Pat. No. 4,215,051). In a specific embodiment described below, Sf9 insect cells are infected with a baculovirus vectors expressing either a 6×HIS-tagged construct, or an (EE)-tagged BRCA1 Modulator construct.

In mammalian host cells, a number of viral-based expression systems may be utilized. Specific embodiments described more fully below express tagged BRCA1 Modulator cDNA sequences using a CMV promoter to transiently express recombinant protein in U937 cells or in Cos-7 cells. Alternatively, retroviral vector systems well known in the art may be used to insert the recombinant expression construct into host cells. For example, retroviral vector systems for transducing hematopoietic cells are described in published PCT applications WO96/09400 and WO94/29438.

In cases where an adenovirus is used as an expression vector, the BRCA1 Modulator nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the BRCA1 Modulator gene product in infected hosts. (E.g., See Logan & Shenk, 1984, Proc. Natl. Acad. Sci. USA 81: 3655–3659). Specific initiation signals may also be required for efficient translation of inserted BRCA1 Modulator nucleotide sequences. These signals include the ATG initiation codon and adjacent sequences. In cases where an entire BRCA1 Modulator gene or cDNA, including its own initiation codon and adjacent sequences, is inserted into the appropriate expression vector, no additional translational control signals may be needed. However, in cases where only a portion of the BRCA1 Modulator coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153: 516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript may be used. Such mammalian host cells include but are not limited. to CHO, VERO, BHK, HeLa, COS, MDCK, 293, 3T3, WI38, and U937 cells.

For long-term, high-yield production of recombinant proteins, stable expression is preferred. For example, cell lines which stably express the BRCA1 Modulator sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form colonies which in turn can be cloned and expanded into cell lines. This method may advantageously be used to engineer cell lines which express the BRCA1 Modulator gene product. Such engineered cell lines may be particularly useful in screening and evaluation of compounds that affect the endogenous activity of the BRCA1 Modulator gene product.

A number of selection systems may be used, including but not limited to the herpes simplex virus thymidine kinase (Wigler et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy et al., 1980, Cell 22: 817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Natl. Acad. Sci. USA 77: 3567; O'Hare et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072); neo, which confers resistance to the aminoglycoside G418 (Colberre-Garapin et al., 1981, J. Mol. Biol. 150: 1); and hygro, which confers resistance to hygromycin (Santerre et al., 1984, Gene 30: 147).

The BRCA1 Modulator gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate BRCA1 Modulator transgenic animals.

Any technique known in the art may be used to introduce the BRCA1 Modulator transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82: 6148–6152); gene targeting in embryonic stem cells (Thompson et al., 1989, Cell 56: 313–321); electroporation of embryos (Lo, 1983, Mol Cell. Biol. 3: 1803–1814); and sperm-mediated gene transfer (Lavitrano et al., 1989, Cell 57: 717–723); etc. For a review of such techniques, see Gordon, 1989, Transgenic Animals, Intl. Rev. Cytol. 115: 171–229, which is incorporated by reference herein in its entirety.

The present invention provides for transgenic animals that carry the BRCA1 Modulator transgene in all their cells, as well as animals which carry the transgene in some, but not all their cells, i.e., mosaic animals. The transgene may be integrated as a single transgene or in concatamers, i.e., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the BRCA1 Modulator transgene be integrated into the chromosomal site of the endogenous BRCA1 Modulator gene, gene targeting is preferred. Briefly, when such a technique is to be utilized, vectors containing some nucleotide sequences homologous to the endogenous BRCA1 Modulator gene are designed for the purpose of integrating, via homologous recombination with chromosomal sequences, into and disrupting the function of the nucleotide sequence of the endogenous BRCA1 Modulator gene. In this way, the expression of the endogenous BRCA1 Modulator gene may also be eliminated by inserting non-functional sequences into the endogenous gene. The transgene may also be selectively introduced into a particular cell type, thus inactivating the endogenous BRCA1 Modulator gene in only that cell type, by following, for example, the teaching of Gu et al. (Gu et al., 1994, Science 265: 103–106). The regulatory sequences required for such a cell-type specific inactivation will depend upon the particular cell type of interest, and will be apparent to those of skill in the art.

Once transgenic animals have been generated, the expression of the recombinant BRCA1 Modulator gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of cell type samples obtained from the animal, in situ hybridization analysis, and RT-PCR. Samples of BRCA1 Modulator gene-expressing tissue, may also be evaluated immunocytochemically using antibodies specific for the BRCA1 Modulator transgene product, as described below.

Antibodies to BRCA1 Modulator Proteins

Antibodies that specifically recognize one or more epitopes of a BRCA1 Modulator Protein, or epitopes of conserved variants, or peptide fragments are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of the BRCA1 Modulator Protein in a biological sample and may, therefore, be utilized as part of a diagnostic or prognostic technique whereby patients may be tested for abnormal amounts of these proteins. Such antibodies may also be utilized in conjunction with, for example, compound screening schemes, as described herein for the evaluation of the effect of test compounds on expression and/or activity of the BRCA1 Modulator Protein.

Additionally, such antibodies can be used in conjunction with the gene therapy techniques described herein, to, for example, evaluate the normal and/or engineered BRCA1 Modulator Protein expressing cells prior to their introduction into the patient. Such antibodies may additionally be used as a method for the inhibition of abnormal BRCA1 Modulator Protein activity.

For the production of antibodies, various host animals may be immunized by injection with the BRCA1 Modulator Protein, a BRCA1 Modulator Protein peptide, truncated BRCA1 Modulator Protein polypeptides, functional equivalents of the BRCA1 Modulator Protein or mutants of the BRCA1 Modulator Protein. Such host animals may include but are not limited to rabbits, mice, and rats, to name but a few. Various adjutants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256: 495–497; and U.S. Pat. No. 4,376,110), the human B-cell hybridoma technique (Kosbor et al., 1983, Immunology Today 4: 72; Cole et al., 1983, Proc. Natl. Acad. Sci. USA 80: 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA, 81: 6851–6855; Neuberger et al., 1984, Nature, 312: 604–608; Takeda et al., 1985, Nature, 314: 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a mAb and a human immunoglobulin constant region.

Alternatively, techniques described for the production of single chain antibodies (U.S. Pat. No. 4,946,778; Bird, 1988, Science 242: 423–426; Huston et al., 1988, Proc. Natl. Acad. Sci. USA 85: 5879–5883; and Ward et al., 1989, Nature 334: 544–546) can be adapted to produce single chain antibodies against BRCA1 Modulator Protein gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246: 1275–1281) to allow rapid and easy identification of monoclonal Fab fragments with the desired specificity.

Antibodies to the BRCA1 Modulator Protein can, in turn, be utilized to generate anti-idiotype antibodies that "mimic" the BRCA1 Modulator Protein using techniques well known to those skilled in the art. (See, e.g., Greenspan & Bona, 1993, FASEB J 7(5): 437–444; and Nissinoff, 1991, J. Immunol. 147(8): 2429–2438).

Identification of Compounds that Increase BRCA1 Levels using BRCA1 Modulators

The BRCA1 gene encodes a protein that has been shown to have tumor suppressor activity. See, Holt, J. T., et al, (1996) Nat. Genet. vol. 12, pages 298–302. Such studies have shown that certain cancer cells have low levels of BRCA1, and that increasing the levels causes a reversion to the normal cell phenotype. Thus, compounds that increase BRCA1 levels will have significant therapeutic use for the treatment of cancer.

An aspect of the instant invention is the description of an assay using BRCA1 and BRCA1 Modulators that facilitates the identification of compounds that increase intracellular levels of BRCA1. One format of the assay is shown in schematic form in FIG. 4. Briefly, the assay makes use of two events: firstly, BRCA1 is known to be a general transcriptional activator, and secondly, BRCA1 Modulators bind to BRCA1. The assay makes use of certain features of the two-hybrid assay described above. Two plasmids are constructed and transfected into a suitable cell line, preferrably a breast or ovarian cell line. A preferred breast cell line would be MCF-7. One plasmid contains the nucleotide sequence recognized by GAL4 operably linked to an activator sequence, and a reporter gene downstream of this sequence. An example of a preferred reporter gene is the gene that encodes luciferase. The second plasmid encodes and expresses the GAL4 DNA binding domain fused to a BRCA1 Modulator. The preferred Modulator is 091-21A31, Sequence ID No. 1.

The GAL4 DNA binding domain-BRCA1 Modulator fusion protein binds to the GAL4 DNA binding domain on the first plasmid which, in turn, recruits any BRCA1 present to form a complex consisting of GAL4 DNA binding domain-BRCA1 Modulator fusion and BRCA1. As part of the complex, BRCA1 is in proximity to the activator sequence which in turn initiates transcription of the reporter gene. Thus, compounds can be tested for their capacity to stimulate the production of BRCA1. Those that do will cause an increase in the reporter gene product. The above assay is schematically presented in FIG. 4.

Identification of Compounds that alter BRCA1 Interaction with BRCA1 Modulators

As mentioned above, BRCA1 is a known tumor suppressor. See, Holt, J. T., et al, (1996) Nat. Genet. vol. 12, pages 298–302. Thus compounds that affect the normal interaction of BRCA1 with BRCA1 Modulator Proteins may affect the tumor suppressor activity of BRCA1. The extent of the effect will, in large part, depend on the chemical properties of the compounds tested. Some may strongly disrupt the interaction of BRCA1 with BRCA1 Modulator Proteins, while others would have a minimal effect. The former would be reflected in a biological assay for altered tumorgenicity, while the latter would not. The converse is also true, certain compounds may strengthen the interaction of BRCA1 with BRCA1 Modulator Proteins, in which case the opposite biological effect would be anticipated. Thus, it is highly desirable to assay for compounds that affect BRCA1 interactions with BRCA1 Modulator Protein.

The basic principle of the assay systems used to identify such compounds that affect BRCA1 interactions with BRCA1 Modulator Proteins involves preparing a reaction mixture containing BRCA1 protein, polypeptide, peptide or fusion protein as described above, and a BRCA1 Modulator Protein under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the BRCA1 moiety and its BRCA1 Modulator Protein. Control reaction mixtures are incubated without the test compound or with a placebo. The formation of any complexes between the BRCA1 moiety and the BRCA1 Modulator Protein is then detected. The formation of a complex in the control reaction, but not in the reaction mixture containing the test compound, indicates that the compound interferes with the interaction of the BRCA1 and the interactive BRCA1 Modulator Protein. Additionally, complex formation within reaction mixtures containing the test compound and normal BRCA1 protein may also be compared to complex formation within reaction mixtures containing the test compound and a mutant BRCA1. This comparison may be important in those cases wherein it is desirable to identify compounds that disrupt interactions of mutant but not normal BRCA1.

The assay for compounds that interfere with the interaction of the BRCA1 and BRCA1 Modulator Proteins can be conducted in a heterogeneous or homogeneous format. Heterogeneous assays involve anchoring either the BRCA1 moiety or the BRCA1 Modulator Protein onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i by adding the test substance to the reaction mixture prior to or simultaneously with the BRCA1 moiety and interactive BRCA1 Modulator Protein. Alternatively, test compounds that disrupt preformed complexes, compounds with higher binding constants that displace one of the components from the complex, can be tested by adding the test compound to the reaction mixture after complexes have been formed. Representative formats are described briefly below.

In a heterogeneous assay system, either the BRCA1 moiety or the interactive BRCA1 Modulator Protein, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of BRCA1 or BRCA1 Modulator Protein and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the inused. In this ogeneous assay can be used. In this approach, a preformed complex of the BRCA1 moiety and the interactive BRCA1 Modulator Protein is prepared in which either the BRCA1 or its BRCA1 Modulator Proteins is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt BRCA1/intracellular BRCA1 Modulator Protein interaction can be identified.

In a particular embodiment, a BRCA1 fusion protein can be prepared for immobilization. For example, BRCA1 or a peptide fragment can be fused to a glutathione-S-transferase (GST) gene using a fusion vector, such as pGEX-5X-1, in such a manner that its binding activity is maintained in the resulting fusion protein. The interactive BRCA1 Modulator Protein can be purified and used to raise a monoclonal antibody, using methods routinely practiced in the art and described above. This antibody can be labeled with the radioactive isotope $^{125}$I, for example, by methods routinely practiced in the art. In a heterogeneous assay, e.g., the GST-BRCA1 fusion protein can be anchored to glutathione-agarose beads. The interactive BRCA1 Modulator Protein can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the BRCA1 protein and the interactive BRCA1 Modulator Protein can be detected by measuring the amount of radioactivity that remains associated with the glutathione-agarose beads. A successful inhibition of the interaction by the test compound will result in a decrease in measured radioactivity.

Alternatively, the GST-BRCA1 fusion protein and the interactive BRCA1 Modulator Protein can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the BRCA1/BRCA1 Modulator Protein interaction can be detected by adding the labeled antibody and measuring the radioactivity associated with the beads.

In another embodiment of the invention, these same techniques can be employed using peptide fragments that correspond to the binding domains of the BRCA1 and/or the interactive or BRCA1 Modulator in place of one or both of the full length proteins. Any number of methods routinely practiced in the art can be used to identify and isolate the binding domains. Such domains are discussed more fully in the examples, below. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. The two hybrid assay may also be used, as discussed more fully in the examples below. For instance, once the gene coding for the intracellular BRCA1 Modulator Protein is obtained, short gene segments can be engineered to express peptide fragments of the protein, which can then be tested for binding activity and purified or synthesized.

Effective Dose

Toxicity and therapeutic efficacy of compounds identified above that affect the interaction of BRCA1 with BRCA1 Modulator Proteins, and thus affect cell growth can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). Numerous model systems are known to the skilled practitioner of the art that can be employed to test the cell growth properties of the instant compounds including growth of cells in soft agar, and effect on tumors in vivo. Such experiments can be conducted on cells co-transfected with BRCA1 and BRCA1 Modulators.

The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The Examples which follow are illustrative of specific embodiments of the invention, and various uses thereof. They are set forth for explanatory purposes only, and are not to be taken as limiting the invention.

EXAMPLE 1

Identification of cDNAs that Encode BRCA1 Modulator Proteins

BRCA1 modulators were identified initially using the yeast two hybrid assay system described in U.S. Pat. No. 5,283,173, or Chien et al., 1991, Proc. Natl. Acad. Sci. USA, 88: 9578–9582. The assay components are also commercially available from Clontech (Palo Alto, Calif.).

The cDNA encoding human BRCA1 (See, Miki, Y., et al Science, vol. 266: 66–71; and PCT/US95/10202) was digested with MvnI-NheI and the fragment representing BRCA1 amino acids 8–1293 was fused to the GAL4 binding domain in the SmaI-NheI sites of pGBT8 plasmid, which is the pMA424 plasmid of Chien et al. as described in Proc. Natl. Acad. Sci. vol. 88: pages 9578–9582 (1991), modified by the insertion of the sequence 5'-CCGGGGATCCCCATGGCTAGCCATATG-3' between the EcoRI and SalI unique sites. This was transformed into the yeast strain YGH1, and the YGH1 strain carrying the plasmid GAL4-BRCA1 (8–1293) was evaluated for its intrinsic ability to activate the two reporters-growth in histidine minus media and β-galactosidase activity. The YGH1 strain carrying the plasmid GAL4-BRCA1 (8–1293) was able to grow on minus histidine plates but this was controlled by the addition of 7.5 mM 3-amino-1,2,4-Triazole (3AT) to the minus histidine plates and the strain had no detectable β-galactosidase activity. The YGH1 strain carrying the plasmid GAL4-BRCA1 (8–1293) was subsequently transformed with a HeLa cell cDNA library fused to the GAL4 activation domain in the pGAD plasmid (Chien et al., Proc. Natl. Acad. Sci. vol. 88: pages 9578–9582 (1991). When a cDNA encodes a protein that interacts with the BRCA1 protein (amino acids 8–1293), the YGH1 strain is expected to grow in the absence of histidine supplemented with 7.5 mM 3AT and produce β-galactosidase.

Four of the $2.5 \times 10^6$ transformants screened grew in the absence of histidine supplemented with 7.5 mM 3AT and had β-galactosidase activity. The plasmids recovered from these 4 yeast strains were used to re-transform the original YGH1 GAL4-BRCA1 (8–1293) strain. All the plasmids conferred the ability to grow in the absence of histidine supplemented with 7.5 mM 3AT and to produce β-galactosidase. Upon subsequent screening, three of the four were found to have cDNAs that encode Modulator Proteins that clearly bound to BRCA1. One of the plasmids contained the novel cDNA encoding for the BRCA1 Modulator Protein hereinafter termed, 091-21A31, Sequence ID No. 1. The nucleotide and protein sequence are shown in FIG. 1. The calculated molecular weight is about 53 kd, and it has an estimated pI of 9.05. Particularly noteworthy is the presence of a zinc finger domain and a leucine zipper motif.

The nucleotide sequence of the second cDNA and amino acid sequence that it encodes, hereinafter termed, 091-1F84, Sequence ID No. 3, is shown in FIG. 2. Note that this clone displays two leucine zipper domains. The protein has a calculated molecular weight of 96,443.3 and an estimated pI of 4.95.

The nucleotide sequence of the third cDNA and amino acid sequence that it encodes, hereinafter termed, 091-132Q20, Sequence ID No. 5, is shown in FIG. 3. Note that this clone also displays a leucine zipper domain. The protein has a calculated molecular weight of 45,904.9 and an estimated pI of 6.73.

EXAMPLE 2

Binding of BRCA1 Domains to BRCA1 Modulators

Experiments were conducted to ascertain which regions of BRCA1 interact with the three BRCA1 Modulators described in Example 1. The experiment was conducted using the two-hybrid assay as described in U.S. Pat. No. 5,283,173, or Chien et al., 1991, Proc. Natl. Acad. Sci. USA, 88: 9578–9582. The cDNA that encodes the 091-1F84, Sequence ID No. 3, 091-21A31, Sequence ID No. 1, and 091-132Q20, Sequence ID No. 5 was fused to the GAL4 activation domain, and those regions of BRCA1 shown in Table 1 and that contain BRCA1 amino acids 1–300, 1–600, or 8–1293 were fused to the binding domain of GAL4. Controls consisted of the vector, or bcl2 fused to the GAL4 binding domain (See, U.S. Pat. 5,539,085).

TABLE 1

INTERACTION OF BRCA1 WITH TWO HYBRID HITS (091-)

| GAL4AD | 1 | 21 | 132 |
|---|---|---|---|
| GAL4BD | F84 | A31 | Q20 |
| BRCA1 (1–300) | − | − | − |
| BRCA1 (1–600) | ++ | ++ | ++ |
| BRCA1 (8–1293) | +++ | +++ | +++ |
| vector or BCL2 | − | − | − |

The BRCA1 constructs employed in the above studies were generated using restriction fragments of BRCA1, and cloning them into the plasmid pGBT8, which is a derivative of the plasmid pMA424, as described by Chien et al. in Proc. Natl. Acad. Sci. vol. 88: pages 9578–9582 (1991), modified by the insertion of the sequence 5'-CCGGGGATCCCCATGGCTAGCCATATG-3' between the EcoRI and SalI unique sites. Briefly, the construct containing the first 300 amino acids of BRCA1 was generated by subcloning the Nco1-EcoR1 blunted BRCA1 fragment into the blunted EcoR1 site of pGBT8. The BRCA1 containing amino acids 8–1293 was generated as described above. Lastly, the BRCA1 construct containing amino acids 1–600 was generated by subcloning the Nco1-Spe1 BRCA1 fragment into the Nco1-Nhe1 site of pGBT8.

Table 1 shows those regions of BRCA1 that interact with the proteins encoded by 091-1F84, Sequence ID No. 3, 091-21A31, Sequence ID No. 1, and 091-132Q20, Sequence ID No. 5. The "+" sign is a subjective measure of the amount of b-galactosidase activity. One "+" being the lowest, and three "+++" being the highest activity. It is apparent from Table 1 that the first 300 amino acids of BRCA1 do not bind to any of the three BRCA1 Modulators, but that all three BRCA1 Modulators bind to the BRCA1 construct containing the first 600 amino acids of BRCA. None of the BRCA1 Modulators bind to the vector or bcl-2 controls, while all the BRCA1 Modulators bound to the near full length BRCA1 construct which has amino acids 8–1293.

The results show that the three BRCA1 Modulators preferentially bind to the first 600 amino acids of BRCA1.

EXAMPLE 3

Identification of Interacting Domains of 091-21A31, Sequence ID No. 1 and BRCA1

Two hybrid experiments were conducted to ascertain the regions of the BRCA1 Modulator 091-21A31, Sequence ID No. 1 that interact with BRCA1. The assay was run essentially as described in Example 1. Transformation and growth of yeast cultures were performed essentially as described in U.S. Pat. No. 5,283,173; Chien et al., 1991, Proc. Natl. Acad. Sci. USA, 88: 9578–9582; or Spaargaren, M., et al., (1994) Biochem. J. 300, 303–307.

Briefly, the YGH1 yeast strain was co-transformed with cDNA encoding 091-21A31, Sequence ID No. 1, or cDNA encoding 091-21A31, Sequence ID No. 1 fragments; containing amino acids 78–469, 1–300, or 300–469 fused to the GAL4 activation domain. As a control, bcl-2 cDNA (See, U.S. Pat. No. 5,539,085) was fused to the GAL4 activation domain. cDNAs encoding BRCA1 fragments having amino acids 1–300, 1–600, or 8–1293 were fused to the GAL4 binding domain as described in Example 2.

The 091-21A31, Sequence ID No. 1 constructs were generated using the plasmids pGADGH or pGAD424; both are available from Clontech.

The 091-21A31, Sequence ID No. 1 construct containing amino acids 75–469 was generated by subcloning the EcoR1-Xho1 091-21A31, Sequence ID No. 1 fragment into the EcoR1-Sal1 site of pGAD424.

The 091-21A31, Sequence ID No. 1 construct containing amino acids 1–300 was generated by subcloning the BamH1-Sal1 091-21A31, Sequence ID No. 1 fragment into the BamH1-Sal1 site of pGADGH.

The 091-21A31, Sequence ID No. 1 construct containing amino acids 300–469 was generated by subcloning the BamH1 blunted-Sal1 091-21A31, Sequence ID No. 1 fragment into the Sal1 blunted-Xho1 site of pGADGH.

Table 2 shows the results of the co-transformation studies. It is apparent that the first 300 amino acids of BRCA1 do not to bind to any of three 091-21A31, Sequence ID No. 1 fragment constructs, nor to 091-21A31, Sequence ID No. 1. The BRCA1 construct containing amino acids 1–600 does bind to 091-21A31, Sequence ID No. 1, and to the construct containing 091-21A31, Sequence ID No. 1 amino acids 78–469, but not to the amino acid 091-21A31, Sequence ID No. 1 constructs 1–300 and 300–469. Also, the BRCA1 construct having amino adds 8–1293 also binds 091-21A31, Sequence ID No. 1, the 78–469 and 1–300 amino acid constructs, but not to the 091-21A31, Sequence ID No. 1 construct having amino acids 300–469.

TABLE 2

INTERACTION OF BRCA1 WITH 091-21

| GAL4AD | 21 | 21 | 21 | 21 |
|---|---|---|---|---|
| GAL4BD | A31 | (78–469) | (1–300) | (300–469) |
| BRCA1 (1–300) | − | − | − | − |
| BRCA1 (1–600) | ++ | ++ | − | − |
| BRCA1 (8–1293) | +++ | +++ | +++ | − |
| vector or BCL2 | − | − | − | − |

EXAMPLE 4

Expression and Purification of BRCA1 Modulators

The BRCA1 Modulators were expressed in and purified from baculovirus SF9 infected cells. Methods for producing baculovirus, as well as growing SF9 cells are well known in the art, and detailed procedures can be found in M. Summers and G. Smith in "A Manual of Methods for Baculovirus Vectors and Insect Cell Culture Procedures," Texas Agricultural Experiment Station, Bulletin No. 1555 (May, 1987 or in EPS 127,839 to G. E. Smith and M. D. Summers.

The following constructs were generated using pAcC13 (See, Rubinfeld, B., et al. Cell 65, 1033–1042 (1991)) or pAcOG, a derivative of pAcC13 in which the polylinker was replaced with a synthetic linker engineered to encode an initiating methionine, the Glu-Glu (See, Grussenmyer, T., et al. Proc. Natl. Acad. Sci. U.S.A. 82, 7952 (1985)) epitope tag, and a multiple cloning site containing several stop codons (See, Rubinfeld, B., et al. J. Biol. Chem, 270, 5549–5555 (1995)).

The construct containing 091-21A31, Sequence ID No. 1 was generated by subcloning the Kpn1-Xba1 091-21A31, Sequence ID No. 1 fragment into pAcC13 at the Kpn1-Xba1 site.

The construct containing 091-1F84, Sequence ID No. 3 was generated by subcloning the Nco1-Xba1 091-1F84, Sequence ID No. 3 fragment into pAcOG1 at the Nco1-Xba1 sites.

The construct containing 091-132Q20, Sequence ID No. 5 was generated by subcloning the Kpn1-Xba1 fragment of 091-132Q20, Sequence ID No. 5 into pAcC13 at the Kpn1-Xba1 site.

Baculovirus containing the appropriate BRCA1 Modulator was produced by transfecting the above described plasmids into SF9 cells, and isolating the corresponding baculovirus using essentially the methods described in Pharmingen's cat. no. 21100D, BaculoGoldtm/Baculovirus DNA. Virus was isolated from individual plaques, and used to infect Sf9 cells. The cells were grown for 4 days, isolated by centrifugation, and cell extracts made by solubilizing the cell pellet. Briefly, recombinant Sf9 cells were pelleted, lysed in 5 volumes of [20 mM Tris (pH 8.0), 1 mM EDTA, 10 µg/ml each of leupeptin, pepstatin, pefabloc, 1 mM aprotinin and 1 mM DTT] and incubated on ice for 10 minutes. NaCl was then added to a final concentration of 150 mM, incubated at room temperature for 10 minutes and centrifuged. The resulting supernatant was loaded onto a 1 ml affinity column containing a mouse Glu-Glu monoclonal antibody covalently cross-linked to protein G-Sepharose. See, Grussenmyer, T., et al., Proc. Natl. Acad. Sci. U.S.A. vol. 82, pp. 7952–7954 (1985). The column was washed with 10–15 ml of lysis buffer and eluted with 100 µg of Glu-Glu peptide (EYMPME) per ml in the same buffer. Fractions were collected and analyzed by sodium dodecyl sulfate-polyacrylamide gel electrophoresis (SDS-PAGE), the peak fractions were pooled and based on purity subjected to further purification on HPLC columns which include Resource Q, Resource S and Resource Eth (Pharmacia). For purification of insoluble proteins, in particular 091-21A31, Sequence ID No. 1, recombinant Sf9 cells were pelleted, lysed in 5 volumes of [20 mM Tris (pH 8.0), 137 mM NaCl, 1 mM EGTA, 1.5 mM MgCl$_2$, 2% SDS, 10 µg/ml each of leupeptin, pepstatin, pefabloc, 1 mM aprotinin and 1 mM DTT], incubated at room temperature for 20–30 minutes and ultra centifuged. The upper phase was removed, NaCl was adjusted to 400 mM and recentrifuged. The clarified supernatent was then diluted 1:10 in 1×TG buffer [20 mM Tris (pH 8.0), 137 mM NaCl, 1 mM EGTA, 1.5 mM MgCl$_2$, 1% Triton ×100, 10% glycerol, 10 µg/ml each of leupeptin, pepstatin, pefabloc, 1 mM aprotinin and 1 mM DTT], filtered through a 3 uM Gelman Versapore filter and loaded onto a 1-ml anti-Glu-Glu affinity column. See, Rubinfeld, B., et al., Mol. Cell. Bio. 12, 4634–4642 (1992). The column was washed with 10–15 ml of 1×TG buffer with 400 mM NaCl and eluted in 1×TG buffer with 1% SDS and 100 µg/ml Glu-Glu peptide. Fractions were analyzed by SDS-PAGE.

EXAMPLE 5

Confirmation of BRCA1 Modulator Protein Binding to BRCA1

To confirm the results of the two-hybrid assays described in Example 1 and further establish the binding of each of the BRCA1 Modulators to BRCA1, two BRCA1 constructs were generated and tested for BRCA1 Modulator binding. The BRCA1 constructs were Glu-Glu tagged BRCA1 5' (1–1293), and BRCA1 3' (1293–1863). The Glu-Glu epitope tag facilitated immunoaffinity purification as described in the above examples. A control construct consisted of rap-GAP. This construct was made as described by Rubinfeld, B. and Polakis P., "Purification of Baculovirus-Produced Rap1 GTPase-activating Proteins". In: Methods and Enzymology, W. E. Balch, Channing J. Der and Alan Hall, Eds., California: Academic Press, Inc., 255, 31–38. The BRCA1 constructs were generated as follows:. pAcO BRCA1 5' (1–1293) was generated by subcloning the NcoI-Nhe1 BRCA1 fragment into pAcO G1S NcoI-Nhe1 sites. pAcO BRCA1 3' (1293–1863) was generated by subcloning the Nhe1 blunted-Not1 BRCA1 fragment into pAcO G2 StuI-Not1 sites. Using standard methods, the constructs were transfected into Sf9 cells. The BRCA1 constructs were purified using the immunoaffinity purification methods essentially as described in the preceding Examples.

For in vitro transcription/translation of the BRCA1 Modulators, the following constructs were subcloned into PCANmyc, a derivative of pCDNA3 (Invitrogen) in which the polylinker was replaced with a synthetic linker engineered to encode an initiating methionine, the Myc (See, Evan, G., et al. Mol. Cell. Biol. 5, 3610 (1985)) epitope tag, and a multiple cloning site (See, Rubinfeld, B., et al. Science, 272, 1023–1026 (1996)).

The plasmid containing the BRCA1 Modulator 091-1F84, Sequence ID No. 3, PCAN myc 091-1F84, Sequence ID No. 3, was generated by subcloning the Spe1 blunted Xho1 091-1F84, Sequence ID No. 3 fragment into PCAN myc3 EcoRV-Xho1 sites. The plasmid containing the BRCA1 Modulator 091-21A31, Sequence ID No. 1, PCAN myc 091-21A31, Sequence ID No. 1, was generated by subcloning the BamH1-Xho1 091-21A31, Sequence ID No. 1 fragment into PCAN myc3 BamH1-Xho1 sites. Lastly, the plasmid containing the BRCA1 Modulator 091-132Q20, Sequence ID No. 5, PCAN myc 091-132Q20, Sequence ID No. 5, was generated by subcloning the EcoR1-Xho1 091-132Q20, Sequence ID No. 5 fragment into PCAN myc3 EcoR1-Xho1 sites.

For in vitro binding analysis, the BRCA1 Modulator cDNAs (091-1F84, Sequence ID No. 3, 091-21A31, Sequence ID No. 1, 091-132Q20, Sequence ID No. 5) were transcribed and translated in vitro in the presence of [$^{35}$S] Methionine using the TNT-coupled wheat germ cell lysate system (Promega). Next, one-two µg of purified recombinant BRCA1 protein, either Glu-Glu tagged BRCA1 5' (1–1293), or BRCA1 3' (1293–1863) was added to 25 µl of precleared lysate along with 10 µl of anti-Glu Glu coupled protein G-Sepharose beads. Following a 2 hour incubation with rocking at 4° C., the beads were washed three times with 1 ml each of ice cold buffer B (20 mM tris pH 7.5, 150 mM NaCl, 0.5% Nonidet P-40), eluted with 20 μl of SDS-PAGE sample buffer and subjected to SDS-PAGE and fluorography.

SDS-PAGE fluorography revealed that all three of the BRCA1 Modulators were affinity precipitated with the construct BRCA1 5' (1–1293) but not BRCA1 3' (1293–1863). The rapGAP control also did not affinity precipitate any of the three BRCA1 Modulators. Taken together these results confirm and extend the results of the two hybrid assay, and establishes that the BRCA1 Modulator proteins interact with BRCA1.

EXAMPLE 6

Preparation of Antibody to BRCA1 Modulators

For antibody production, immunoaffinity purification of BRCA1 Modulators from baculovirus infected Sf9 insect cells was performed with immobilized anti-Glu-Glu antibody specific for the Glu-Glu epitope tag expressed on the recombinant soluble proteins (See, Rubinfeld, B., et al., Mol. Cell. Bio. 12, 4634–4642 (1992)). Briefly, recombinant Sf9 cells were pelleted, lysed in 5 volumes of [20 mM Tris (pH 8.0), 1 mM EDTA, 10 μg/ml each of leupeptin, pepstatin, pefabloc, 1 Mm aprotinin and 1 mM DTT] and incubated on ice for 10 minutes. NaCl was then added to a final concentration of 150 mM, incubated at room temperature for 10 minutes and centrifuged. Then resulting supernatant was loaded onto a 1-ml affinity column containing the Glu-Glu antibody covalently cross-linked to protein G-Sepharose. The column was washed with 10–15 ml of lysis buffer and eluted with 100 μg of Glu-Glu peptide (EYMPME) per ml in the same buffer. Fractions were collected and analyzed by sodium dodecyl sulfatepolyacrylamide gel electrophoresis (SDS-PAGE), the peak fractions were pooled and based on purity subjected to further purification on HPLC columns which include Resource Q, Resource S and Resource Eth (Pharmacia). For purification of insoluble proteins, in particular 21, recombinant Sf9 cells were pelleted, lysed in 5 volumes of [20 mM Tris (pH 8.0), 137 mM NaCl, 1 mM EGTA, 1.5 mM $MgCl_2$, 2% SDS, 10 μg/ml each of leupeptin, pepstatin, pefabloc, 1 mM aprotinin and 1 mM DTT], incubated at room temperature for 20–30 minutes and ultra centifuged. The upper phase was removed, NaCl was adjusted to 400 mM and recentrifuged. The clarified supernatent was then diluted 1:10 in 1×TG buffer [20 mM Tris (pH 8.0), 137 mM NaCl, 1 mM EGTA, 1.5 mM $MgCl_2$, 1% Triton ×100, 10% glycerol, 10 μg/ml each of leupeptin, pepstatin, pefabloc, 1 mM aprotinin and 1 mM DTT], filtered through a 3 μm Gelman Versapore filter and loaded onto a 1-ml anti-Glu-Glu affinity column. The column was washed with 10–15 ml of 1×TG buffer with 400 mM NaCl and eluted in 1×TG buffer with 1% SDS ,md 100 μg/ml Glu-Glu peptide. Fractions were analyzed by SDS-PAGE, pooled and used to immunize rabbits.

To produce antisera containing antibodies directed against the BRCA1 Modulators the latter are used to immunize rabbits as follows. For the BRCA1 Modulator 091-21A31, Sequence ID No. 1, the immunization protocol generally consisted of two immunizations; the first was a subcutaneous injection of 0.500 mg in CFA, followed by a second intramuscular injection of 0.250 mg about four weeks later in ICFA. The rabbits were bled, antisera collected and antibody purified as setforth below.

BRCA1 Modulator antibodies are affinity purified using BRCA1 Modulator immunogens which have been coupled to a support matrix. Briefly, the BRCA1 Modulator 091-21A31, Sequence ID No. 1 is coupled to CNBr activated Sepharose 6MB (Pharmacia) as follows. One ml of matrix was activated according to manufacturer's instructions (ie. resuspended in 1 mM H Cl, washed for 15 min. in 1 mM HCl on a sintered glass filter). One mg of 091-21A31, Sequence ID No. 1 was dialyzed against coupling buffer [0.1M $NaHCO_3$ pH 8.3, 0.5M NaCl] overnight at 4° C. with two changes of buffer. The dialyzed protein was then incubated with the CNBr activated Sepharose 6MB and incubated with rocking overnight at 4° C. The excess ligand was washed away with coupling buffer and any remaining active groups were blocked with 1M ethanolamine at room temperature for two hours. This material was then washed with three cycles of alternating pH—each cycle consists of a wash with 0.1M acetate buffer, pH 4.0, 0.5M NaCl followed by a wash with 0.1M Tris, pH 8.0, 0.5M NaCl. The protein coupled gel matrix was then resuspended in PBS and incubated with 5 ml of antibody serum with rocking overnight at 4° C. The mixture was poured into a column, allowed to drip through and washed 3 times with 15 ml PBS per wash. Seven elutions with 800 μl of 0.2M glycine, pH 2.5, were collected and each elution was neutralized immediately with 200 μl 1M $K_2HPO_4$. Peak fractions were combined and dialyzed into PBS Azide for storage.

American Type Culture Collection Deposits

The cDNA clones that encode 091-1F84, Sequence ID No. 3, 091-21A31, Sequence ID No. 1, and 091-132Q20, Sequence ID No. 5 were deposited with the American Type Culture Collection (ATCC) on Aug. 14, 1996 under accession numbers 98141 (091-1F84, Sequence ID No. 3), 98142 (091-21A31, Sequence ID No. 1), and 98143 (091-132Q20, Sequence ID No. 5). The deposits were made under the Budapest Treaty and shall be maintained at least 30 years after the date of deposit and 5 years after the date of the most recent request for the deposit the address of the American Type Culture Collection is 10801 University Boulevard, Manassas, Va. 20110-2209, U.S.A.

The invention now being fully described, it will be apparent to one of ordinary skill in the art that many changes and modifications can be made thereto without departing from the spirit or scope of the appended claims.

---

We claim:

1. An isolated nucleic acid sequence that encodes a BRCA1 Modulator Protein wherein said sequence is selected from the group consisting of 091-21A31, Sequence ID No. 1, 091-1F84, Sequence ID No. 3 and 091-132Q20, Sequence ID No. 5.

2. Isolated host cells comprising an isolated nucleic acid sequence of claim 1 that encodes a BRCA1 Modulator Protein.

3. Vectors that comprise an isolated nucleic acid sequence of claim 1 that encodes a BRCA1 Modulator Protein.

4. An isolated nucleic acid sequence that encodes a protein encoded by the cDNA on deposit with the ATCC with accession no. 98141 (091-1F84, Sequence ID No. 3).

5. An isolated nucleic acid sequence that encodes a protein encoded by the cDNA on deposit with the ATCC with accession no. 98142 (091-21A31, Sequence ID No. 1).

6. An isolated nucleic acid sequence that encodes a protein encoded by the cDNA on deposit with the ATCC with accession no. 98143 (091-132Q20, Sequence ID No. 5).

7. An isolated process for producing a BRCA1 Modulator Protein comprising culturing a cell of claim 2 in a suitable culture medium and isolating said protein from said cell or said medium.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:

```
          (A) LENGTH: 2065 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (iv) ANTI-SENSE: NO (ix) FEATURE:
          (A) NAME/KEY: CDS
          (B) LOCATION: 103..1512

(xi) SEQUENCE DESCRIPTION: SEQ ID NO:1:

GTGGATCCCC CGGGCTGCAG GAATTCGGCA CGAGCGGCAC GAGTACGAAG CCGGACCTGT            60

AGCAGTTTCT TTGGCTGCCT GGGCCCCTTG AGTCCAGCCA TC ATG CCT ATC CGT             114
                                              Met Pro Ile Arg
                                                1

GCT CTG TGC ACT ATC TGC TCC GAC TTC TTC GAT CAC TCC CGC GAC GTG            162
Ala Leu Cys Thr Ile Cys Ser Asp Phe Phe Asp His Ser Arg Asp Val
  5              10                  15                  20

GCC GCC ATC CAC TGC GGC CAC ACC TTC CAC TTG CAG TGC CTA ATT CAG            210
Ala Ala Ile His Cys Gly His Thr Phe His Leu Gln Cys Leu Ile Gln
             25                  30                  35

TGG TTT GAG ACA GCA CCA AGT CGG ACC TGC CCA CAG TGC CGA ATC CAG            258
Trp Phe Glu Thr Ala Pro Ser Arg Thr Cys Pro Gln Cys Arg Ile Gln
         40                  45                  50

GTT GGC AAA AGA ACC ATT ATC AAT AAG CTC TTC TTT GAT CTT GCC CAG            306
Val Gly Lys Arg Thr Ile Ile Asn Lys Leu Phe Phe Asp Leu Ala Gln
     55                  60                  65

GAG GAG GAG AAT GTC TTG GAT GCA GAA TTC TTA AAG AAT GAA CTG GAC            354
Glu Glu Glu Asn Val Leu Asp Ala Glu Phe Leu Lys Asn Glu Leu Asp
 70                  75                  80

AAT GTC AGA GCC CAG CTT TCC CAG AAA GAC AAG GAG AAA CGA GAC AGC            402
Asn Val Arg Ala Gln Leu Ser Gln Lys Asp Lys Glu Lys Arg Asp Ser
 85                  90                  95                 100

CAG GTC ATC ATC GAC ACT CTG CGG GAT ACG CTG GAA GAA CGC AAT GCT            450
Gln Val Ile Ile Asp Thr Leu Arg Asp Thr Leu Glu Glu Arg Asn Ala
                105                 110                 115

ACT GTG GTA TCT CTG CAG CAG GCC TTG GGC AAG GCC GAG ATG CTG TGC            498
Thr Val Val Ser Leu Gln Gln Ala Leu Gly Lys Ala Glu Met Leu Cys
            120                 125                 130

TCC ACA CTG AAA AAG CAG ATG AAG TAC TTA GAG CAG CAG CAG GAT GAG            546
Ser Thr Leu Lys Lys Gln Met Lys Tyr Leu Glu Gln Gln Gln Asp Glu
        135                 140                 145

ACC AAA CAA GCA CAA GAG GAG GCC CGC CGG CTC AGG AGC AAG ATG AAG            594
Thr Lys Gln Ala Gln Glu Glu Ala Arg Arg Leu Arg Ser Lys Met Lys
    150                 155                 160

ACC ATG GAG CAG ATT GAG CTT CTA CTC CAG AGC CAG CGC CCT GAG GTG            642
Thr Met Glu Gln Ile Glu Leu Leu Leu Gln Ser Gln Arg Pro Glu Val
165                 170                 175                 180

GAG GAG ATG ATC CGA GAC ATG GGT GTG GGA CAG TCA GCG GTG GAA CAG            690
Glu Glu Met Ile Arg Asp Met Gly Val Gly Gln Ser Ala Val Glu Gln
                185                 190                 195

CTG GCT GTG TAC TGT GTG TCT CTC AAG AAA GAG TAC GAG AAT CTA AAA            738
Leu Ala Val Tyr Cys Val Ser Leu Lys Lys Glu Tyr Glu Asn Leu Lys
            200                 205                 210

GAG GCA CGG AAG GCC TCA GGG GAG GTG GCT GAC AAG CTG AGG AAG GAT            786
Glu Ala Arg Lys Ala Ser Gly Glu Val Ala Asp Lys Leu Arg Lys Asp
        215                 220                 225

TTG TTT TCC TCC AGA AGC AAG TTG CAG ACA GTC TAC TCT GAA TTG GAT            834
```

```
                                                            -continued

Leu Phe Ser Ser Arg Ser Lys Leu Gln Thr Val Tyr Ser Glu Leu Asp
    230                 235                 240

CAG GCC AAG TTA GAA CTG AAG TCA GCC CAG AAG GAC TTA CAG AGT GCT        882
Gln Ala Lys Leu Glu Leu Lys Ser Ala Gln Lys Asp Leu Gln Ser Ala
245                 250                 255                 260

GAC AAG GAA ATC ATG AGC CTG AAA AAG AAG CTA ACG ATG CTG CAG GAA        930
Asp Lys Glu Ile Met Ser Leu Lys Lys Lys Leu Thr Met Leu Gln Glu
                    265                 270                 275

ACC TTG AAC CTG CCA CCA GTG GCC AGT GAG ACT GTC GAC CGC CTG GTT        978
Thr Leu Asn Leu Pro Pro Val Ala Ser Glu Thr Val Asp Arg Leu Val
                280                 285                 290

TTA GAG AGC CCA GCC CCT GTG GAG GTG AAT CTG AAG CTC CGC CGG CCA       1026
Leu Glu Ser Pro Ala Pro Val Glu Val Asn Leu Lys Leu Arg Arg Pro
            295                 300                 305

TCC TTC CGT GAT GAT ATT GAT CTC AAT GCT ACC TTT GAT GTG GAT ACT       1074
Ser Phe Arg Asp Asp Ile Asp Leu Asn Ala Thr Phe Asp Val Asp Thr
310                 315                 320

CCC CCA GCC CGG CCC TCC AGC TCC CAG CAT GGT TAC TAC GAA AAA CTT       1122
Pro Pro Ala Arg Pro Ser Ser Ser Gln His Gly Tyr Tyr Glu Lys Leu
325                 330                 335                 340

TGC CTA GAG AAG TCA CAC TCC CCA ATT CAG GAT GTC CCC AAG AAG ATA       1170
Cys Leu Glu Lys Ser His Ser Pro Ile Gln Asp Val Pro Lys Lys Ile
                    345                 350                 355

TGC AAA GGC CCC AGG AAG GAG TCC CAG CTC TCA CTG GGT GGC CAG AGC       1218
Cys Lys Gly Pro Arg Lys Glu Ser Gln Leu Ser Leu Gly Gly Gln Ser
                360                 365                 370

TGT GCA GGA GAG CCA GAT GAG GAA CTG GTT GGT GCC TTC CCT ATT TTT       1266
Cys Ala Gly Glu Pro Asp Glu Glu Leu Val Gly Ala Phe Pro Ile Phe
            375                 380                 385

GTC CGG AAT GCC ATC CTA GGC CAG AAA CAG CCC AAG AGG CCC AGG TCA       1314
Val Arg Asn Ala Ile Leu Gly Gln Lys Gln Pro Lys Arg Pro Arg Ser
390                 395                 400

GAG TCC TCT TGC AGC AAA GAT GTG GTA AGG ACA GGC TTC GAT GGG CTC       1362
Glu Ser Ser Cys Ser Lys Asp Val Val Arg Thr Gly Phe Asp Gly Leu
405                 410                 415                 420

GGT GGC CGG ACA AAA TTC ATC CAG CCT ACT GAC ACA GTC ATG ATC CGC       1410
Gly Gly Arg Thr Lys Phe Ile Gln Pro Thr Asp Thr Val Met Ile Arg
                    425                 430                 435

CCA TTG CCT GTT AAG CCC AAG ACC AAG GTT AAG CAG AGG GTG AGG GTG       1458
Pro Leu Pro Val Lys Pro Lys Thr Lys Val Lys Gln Arg Val Arg Val
                440                 445                 450

AAG ACA GTG CCT TCT CTC TTC CAG GCC AAG CTG GAC ACC TTC CTG TGG       1506
Lys Thr Val Pro Ser Leu Phe Gln Ala Lys Leu Asp Thr Phe Leu Trp
            455                 460                 465

TCG TGA GAACAGTGAG TCTGACCAAT GGCCAGACAC ATGCCTGCAA CTTGTAGGTC        1562
Ser  *
    470

AAGGACTGTC CAGGCAGGGG TTTTGTGGAC AGAGCCCCAC TTTCGGGACC AGCCTGAGGT     1622

GTAAGGGCAG ACAAACAGGT GAGGGTGAGT GTGACACCCA GAGACTGCTC TTCCTGCCCT     1682

CACCCTGCCC CACTCCTACG ACTGGGAGCT GACATGACCA GCCCACTGAT CCTGTCAGCA     1742

GGTCCTGCTC CTGTTGCCAG GCTCCTGTTT ATAGCCATGA TCAGATGTGG TCAGACTCTT     1802

TCTGGGCCTG GAGACCACGG TCACTTGTTG ACTGTCTCTG TGGACCAGAG TGCTTGAGGC     1862

ATCTCAGGCA GCCTCAGCCC AAGCTTCTAC CTGCCTTTGA CTTGCTTCTA GGCATAGCCT     1922

GGGCCAAGCA GGGTGGGGAA TGGAGGATAG CATGGGATGT ATGGAGAGGA TGGAAGATTT     1982

TCATGTAAAA TAAAATTAAA AAAAAAAAA CAAAAAAAA AAAAAAAA AAAAAAAA           2042

AAAAAAAAAA AAAAAACTC GAG                                             2065
```

(2) INFORMATION FOR SEQ ID NO:2:

(i) SEQUENCE CHARACTERISTICS:
        (A) LENGTH: 469 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Ile Arg Ala Leu Cys Thr Ile Cys Ser Asp Phe Phe Asp His
 1               5                  10                  15

Ser Arg Asp Val Ala Ala Ile His Cys Gly His Thr Phe His Leu Gln
             20                  25                  30

Cys Leu Ile Gln Trp Phe Glu Thr Ala Pro Ser Arg Thr Cys Pro Gln
         35                  40                  45

Cys Arg Ile Gln Val Gly Lys Arg Thr Ile Ile Asn Lys Leu Phe Phe
     50                  55                  60

Asp Leu Ala Gln Glu Glu Asn Val Leu Asp Ala Glu Phe Leu Lys
 65                  70                  75                  80

Asn Glu Leu Asp Asn Val Arg Ala Gln Leu Ser Gln Lys Asp Lys Glu
                 85                  90                  95

Lys Arg Asp Ser Gln Val Ile Ile Asp Thr Leu Arg Asp Thr Leu Glu
            100                 105                 110

Glu Arg Asn Ala Thr Val Val Ser Leu Gln Gln Ala Leu Gly Lys Ala
        115                 120                 125

Glu Met Leu Cys Ser Thr Leu Lys Lys Gln Met Lys Tyr Leu Glu Gln
    130                 135                 140

Gln Gln Asp Glu Thr Lys Gln Ala Gln Glu Glu Ala Arg Arg Leu Arg
145                 150                 155                 160

Ser Lys Met Lys Thr Met Glu Gln Ile Glu Leu Leu Gln Ser Gln
                165                 170                 175

Arg Pro Glu Val Glu Glu Met Ile Arg Asp Met Gly Val Gly Gln Ser
            180                 185                 190

Ala Val Glu Gln Leu Ala Val Tyr Cys Val Ser Leu Lys Lys Glu Tyr
        195                 200                 205

Glu Asn Leu Lys Glu Ala Arg Lys Ala Ser Gly Glu Val Ala Asp Lys
    210                 215                 220

Leu Arg Lys Asp Leu Phe Ser Ser Arg Ser Lys Leu Gln Thr Val Tyr
225                 230                 235                 240

Ser Glu Leu Asp Gln Ala Lys Leu Glu Leu Lys Ser Ala Gln Lys Asp
                245                 250                 255

Leu Gln Ser Ala Asp Lys Glu Ile Met Ser Leu Lys Lys Lys Leu Thr
            260                 265                 270

Met Leu Gln Glu Thr Leu Asn Leu Pro Pro Val Ala Ser Glu Thr Val
        275                 280                 285

Asp Arg Leu Val Leu Glu Ser Pro Ala Pro Val Glu Val Asn Leu Lys
    290                 295                 300

Leu Arg Arg Pro Ser Phe Arg Asp Asp Ile Asp Leu Asn Ala Thr Phe
305                 310                 315                 320

Asp Val Asp Thr Pro Pro Ala Arg Pro Ser Ser Gln His Gly Tyr
                325                 330                 335

Tyr Glu Lys Leu Cys Leu Glu Lys Ser His Ser Pro Ile Gln Asp Val
            340                 345                 350

Pro Lys Lys Ile Cys Lys Gly Pro Arg Lys Glu Ser Gln Leu Ser Leu
```

```
                        355                 360                 365
Gly Gly Gln Ser Cys Ala Gly Glu Pro Asp Glu Glu Leu Val Gly Ala
        370                 375                 380

Phe Pro Ile Phe Val Arg Asn Ala Ile Leu Gly Gln Lys Gln Pro Lys
385                 390                 395                 400

Arg Pro Arg Ser Glu Ser Ser Cys Ser Lys Asp Val Val Arg Thr Gly
                405                 410                 415

Phe Asp Gly Leu Gly Gly Arg Thr Lys Phe Ile Gln Pro Thr Asp Thr
                420                 425                 430

Val Met Ile Arg Pro Leu Pro Val Lys Pro Lys Thr Lys Val Lys Gln
            435                 440                 445

Arg Val Arg Val Lys Thr Val Pro Ser Leu Phe Gln Ala Lys Leu Asp
        450                 455                 460

Thr Phe Leu Trp Ser
465             470

(2) INFORMATION FOR SEQ ID NO:3:

(i) SEQUENCE CHARACTERISTICS:
        (A) LENGTH: 3256 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 34..2541

(xi) SEQUENCE DESCRIPTION: SEQ ID NO:3:

GAACTAGTGG ATCCCCCGGG CTGCAGGAAT TCG GCA CGA GAA AGC TTA TCC CTT      54
                                    Ala Arg Glu Ser Leu Ser Leu
                                     1               5

CCC TCG ATG CTT CGG GAT GCT GCA ATT GGC ACT ACC CCT TTC TCT ACT     102
Pro Ser Met Leu Arg Asp Ala Ala Ile Gly Thr Thr Pro Phe Ser Thr
            10                  15                  20

TGC TCG GTG GGG ACT TGG TTT ACT CCT TCA GCA CCA CAG GAA AAG AGT     150
Cys Ser Val Gly Thr Trp Phe Thr Pro Ser Ala Pro Gln Glu Lys Ser
     25                  30                  35

ACA AAC ACA TCC CAG ACA GGC CTG GTT GGC ACC AAG CAC AGT ACT TCT     198
Thr Asn Thr Ser Gln Thr Gly Leu Val Gly Thr Lys His Ser Thr Ser
 40                  45                  50                  55

GAG ACA GAG CAG CTC CTG TGT GGC CGG CCT CCA GAT CTG ACT GCC TTG     246
Glu Thr Glu Gln Leu Leu Cys Gly Arg Pro Pro Asp Leu Thr Ala Leu
                60                  65                  70

TCT CGA CAT GAC TTG GAA GAT AAC CTG CTG AGC TCT CTT GTC ATT CTG     294
Ser Arg His Asp Leu Glu Asp Asn Leu Leu Ser Ser Leu Val Ile Leu
             75                  80                  85

GAG GTT CTC TCC CGC CAG CTT CGG GAC TGG AAG AGC CAG CTG GCT GTC     342
Glu Val Leu Ser Arg Gln Leu Arg Asp Trp Lys Ser Gln Leu Ala Val
         90                  95                 100

CCT CAC CCA GAA ACC CAG GAC AGT AGC ACA CAG ACT GAC ACA TCT CAC     390
Pro His Pro Glu Thr Gln Asp Ser Ser Thr Gln Thr Asp Thr Ser His
105                 110                 115

AGT GGG ATA ACT AAT AAA CTT CAG CAT CTT AAG GAG AGC CAT GAG ATG     438
Ser Gly Ile Thr Asn Lys Leu Gln His Leu Lys Glu Ser His Glu Met
120                 125                 130                 135

GGA CAG GCC CTA CAG CAG GCC AGA AAT GTC ATG CAA TCA TGG GTG CTT     486
Gly Gln Ala Leu Gln Gln Ala Arg Asn Val Met Gln Ser Trp Val Leu
                140                 145                 150
```

| | | |
|---|---|---|
| ATC TCT AAA GAG CTG ATA TCC TTG CTT CAC CTA TCC CTG TTG CAT TTA<br>Ile Ser Lys Glu Leu Ile Ser Leu Leu His Leu Ser Leu Leu His Leu<br>              155                  160              165 | | 534 |
| GAA GAA GAT AAG ACT ACT GTG AGT CAG GAG TCT CGG CGT GCA GAA ACA<br>Glu Glu Asp Lys Thr Thr Val Ser Gln Glu Ser Arg Arg Ala Glu Thr<br>          170                175                180 | | 582 |
| TTG GTC TGT TGC TGT TTT GAT TTG CTG AAG AAA TTG AGG GCA AAG CTC<br>Leu Val Cys Cys Cys Phe Asp Leu Leu Lys Lys Leu Arg Ala Lys Leu<br>            185                  190              195 | | 630 |
| CAG AGC CTC AAA GCA GAA AGG GAG GAG GCA AGG CAC AGA GAG GAA ATG<br>Gln Ser Leu Lys Ala Glu Arg Glu Glu Ala Arg His Arg Glu Glu Met<br>200                  205                  210              215 | | 678 |
| GCT CTC AGA GGC AAG GAT GCG GCA GAG ATA GTG TTG GAG GCT TTC TGT<br>Ala Leu Arg Gly Lys Asp Ala Ala Glu Ile Val Leu Glu Ala Phe Cys<br>                  220                  225              230 | | 726 |
| GCA CAC GCC AGC CAG CGC ATC AGC CAG CTG GAA CAG GAC CTA GCA TCC<br>Ala His Ala Ser Gln Arg Ile Ser Gln Leu Glu Gln Asp Leu Ala Ser<br>                  235                  240              245 | | 774 |
| ATG CGG GAA TTC AGA GGC CTT CTG AAG GAT GCC CAG ACC CAA CTG GTA<br>Met Arg Glu Phe Arg Gly Leu Leu Lys Asp Ala Gln Thr Gln Leu Val<br>          250                255                260 | | 822 |
| GGG CTT CAT GCC AAG CAA GAA GAG CTG GTT CAG CAG ACA GTG AGT CTT<br>Gly Leu His Ala Lys Gln Glu Glu Leu Val Gln Gln Thr Val Ser Leu<br>            265                  270              275 | | 870 |
| ACT TCT ACC TTG CAA CAA GAC TGG AGG TCC ATG CAA CTG GAT TAT ACA<br>Thr Ser Thr Leu Gln Gln Asp Trp Arg Ser Met Gln Leu Asp Tyr Thr<br>280                  285                  290              295 | | 918 |
| ACA TGG ACA GCT TTG CTG AGT CGG TCC CGA CAA CTC ACA GAG AAA CTC<br>Thr Trp Thr Ala Leu Leu Ser Arg Ser Arg Gln Leu Thr Glu Lys Leu<br>                  300                  305              310 | | 966 |
| ACA GTC AAG AGC CAG CAA GCC CTG CAG GAA CGT GAT GTG GCA ATT GAG<br>Thr Val Lys Ser Gln Gln Ala Leu Gln Glu Arg Asp Val Ala Ile Glu<br>                  315                  320              325 | | 1014 |
| GAA AAG CAG GAG GTT TCT AGG GTG CTG GAA CAA GTC TCT GCC CAG TTA<br>Glu Lys Gln Glu Val Ser Arg Val Leu Glu Gln Val Ser Ala Gln Leu<br>          330                335                340 | | 1062 |
| GAG GAG TGC AAA GGC CAA ACA GAA CAA CTG GAG TTG GAA AAC AGT CGT<br>Glu Glu Cys Lys Gly Gln Thr Glu Gln Leu Glu Leu Glu Asn Ser Arg<br>            345                  350              355 | | 1110 |
| CTA GCA ACA GAT CTC CGG GCT CAG TTG CAG ATT CTG GCC AAC ATG GAC<br>Leu Ala Thr Asp Leu Arg Ala Gln Leu Gln Ile Leu Ala Asn Met Asp<br>360                  365                  370              375 | | 1158 |
| AGC CAG CTA AAA GAG CTA CAG AGT CAG CAT ACC CAT TGT GCC CAG GAC<br>Ser Gln Leu Lys Glu Leu Gln Ser Gln His Thr His Cys Ala Gln Asp<br>                  380                  385              390 | | 1206 |
| CTG GCT ATG AAG GAT GAG TTA TTC TGC CAG CTT ACC CAG AGC AAT GAG<br>Leu Ala Met Lys Asp Glu Leu Phe Cys Gln Leu Thr Gln Ser Asn Glu<br>                395                  400              405 | | 1254 |
| GAG CAG GCT GCT CAA TGG CAA AAG GAA GAG ATG GCA CTA AAA CAC ATG<br>Glu Gln Ala Ala Gln Trp Gln Lys Glu Glu Met Ala Leu Lys His Met<br>          410                415                420 | | 1302 |
| CAG GCA GAA CTG CAG CAG CAA CAA GCT GTC CTG GCC AAA GAG GTG CGG<br>Gln Ala Glu Leu Gln Gln Gln Gln Ala Val Leu Ala Lys Glu Val Arg<br>            425                430                435 | | 1350 |
| GAC CTG AAA GAG ACC TTG GAG TTT GCA GAC CAG GAG AAT CAG GTT GCT<br>Asp Leu Lys Glu Thr Leu Glu Phe Ala Asp Gln Glu Asn Gln Val Ala<br>440                  445                  450              455 | | 1398 |
| CAC CTG GAG CTG GGT CAG GTT GAG TGT CAA TTG AAA ACC ACA CTG GAA<br>His Leu Glu Leu Gly Gln Val Glu Cys Gln Leu Lys Thr Thr Leu Glu<br>                  460                  465              470 | | 1446 |

```
GTG CTC CGG GAG CGC AGC TTG CAG TGT GAG AAC CTC AAG GAC ACT GTA      1494
Val Leu Arg Glu Arg Ser Leu Gln Cys Glu Asn Leu Lys Asp Thr Val
            475                 480                 485

GAG AAC CTA ACG GCT AAA CTG GCC AGC ACC ATA GCA GAT AAC CAG GAG      1542
Glu Asn Leu Thr Ala Lys Leu Ala Ser Thr Ile Ala Asp Asn Gln Glu
            490                 495                 500

CAA GAT CTG GAG AAA ACA CGG CAG TAC TCT CAA AAG CTA AGG CTG CTG      1590
Gln Asp Leu Glu Lys Thr Arg Gln Tyr Ser Gln Lys Leu Arg Leu Leu
            505                 510                 515

ACT GAG CAA CTA CAG AGC CTG ACT CTC TTT CTA CAG ACA AAA CTA AAG      1638
Thr Glu Gln Leu Gln Ser Leu Thr Leu Phe Leu Gln Thr Lys Leu Lys
520                 525                 530                 535

GAG AAG ACT GAA CAA GAG ACC CTT CTG CTG AGT ACA GCC TGT CCT CCC      1686
Glu Lys Thr Glu Gln Glu Thr Leu Leu Leu Ser Thr Ala Cys Pro Pro
                540                 545                 550

ACC CAG GAA CAC CCT CTG CCT AAT GAC AGG ACC TTC CTG GGA AGC ATC      1734
Thr Gln Glu His Pro Leu Pro Asn Asp Arg Thr Phe Leu Gly Ser Ile
                555                 560                 565

TTG ACA GCA GTG GCA GAT GAA GAG CCA GAA TCA ACT CCT GTG CCC TTG      1782
Leu Thr Ala Val Ala Asp Glu Glu Pro Glu Ser Thr Pro Val Pro Leu
                570                 575                 580

CTT GGA AGT GAC AAG AGT GCT TTC ACC CGA GTA GCA TCA ATG GTT TCC      1830
Leu Gly Ser Asp Lys Ser Ala Phe Thr Arg Val Ala Ser Met Val Ser
585                 590                 595

CTT CAG CCC GCA GAG ACC CCA GGC ATG GAG GAG AGC CTG GCA GAA ATG      1878
Leu Gln Pro Ala Glu Thr Pro Gly Met Glu Glu Ser Leu Ala Glu Met
600                 605                 610                 615

AGT ATT ATG ACT ACT GAG CTT CAG AGT CTT TGT TCC CTG CTA CAA GAG      1926
Ser Ile Met Thr Thr Glu Leu Gln Ser Leu Cys Ser Leu Leu Gln Glu
                620                 625                 630

TCT AAA GAA GAA GCC ATC AGG ACT CTG CAG CGA AAA ATT TGT GAG CTG      1974
Ser Lys Glu Glu Ala Ile Arg Thr Leu Gln Arg Lys Ile Cys Glu Leu
            635                 640                 645

CAA GTT AGG CTG CAG GCC CAG GAA GAA CAG CAT CAG GAA GTC CAG AAG      2022
Gln Val Arg Leu Gln Ala Gln Glu Glu Gln His Gln Glu Val Gln Lys
            650                 655                 660

GCA AAA GAA GCA GAC ATA GAG AAG CTG AAC CAG GCC TTG TGC TTG CGC      2070
Ala Lys Glu Ala Asp Ile Glu Lys Leu Asn Gln Ala Leu Cys Leu Arg
665                 670                 675

TAC AAG AAT GAA AAG GAG CTC CAG GAA GTG ATA CAG CAG CAG AAT GAG      2118
Tyr Lys Asn Glu Lys Glu Leu Gln Glu Val Ile Gln Gln Gln Asn Glu
680                 685                 690                 695

AAG ATC CTA GAA CAG ATA GAC AAG AGT GGC GAG CTC ATA AGC CTT AGA      2166
Lys Ile Leu Glu Gln Ile Asp Lys Ser Gly Glu Leu Ile Ser Leu Arg
                700                 705                 710

GAG GAG GTG ACC CAC CTT ACC CGC TCA CTT CGG CGT GCG GAG ACA GAG      2214
Glu Glu Val Thr His Leu Thr Arg Ser Leu Arg Arg Ala Glu Thr Glu
                715                 720                 725

ACC AAA GTG CTC CAG GAG GCC CTG GCA GGC CAG CTG GAC TCC AAC TGC      2262
Thr Lys Val Leu Gln Glu Ala Leu Ala Gly Gln Leu Asp Ser Asn Cys
            730                 735                 740

CAG CCT ATG GCC ACC AAT TGG ATC CAG GAG AAA GTG TGG CTC TCT CAG      2310
Gln Pro Met Ala Thr Asn Trp Ile Gln Glu Lys Val Trp Leu Ser Gln
745                 750                 755

GAG GTG GAC AAA CTG AGA GTG ATG TTC CTG GAG ATG AAA AAT GAG AAG      2358
Glu Val Asp Lys Leu Arg Val Met Phe Leu Glu Met Lys Asn Glu Lys
760                 765                 770                 775

GAA AAA CTC ATG ATC AAG TTC CAG AGC CAT AGA AAT ATC CTA GAG GAG      2406
Glu Lys Leu Met Ile Lys Phe Gln Ser His Arg Asn Ile Leu Glu Glu
                780                 785                 790
```

```
AAC CTT CGG CGC TCT GAC AAG GAG TTA GAA AAA CTA GAT GAC ATT GTT        2454
Asn Leu Arg Arg Ser Asp Lys Glu Leu Glu Lys Leu Asp Asp Ile Val
            795                 800                 805

CAG CAT ATT TAT AAG ACC CTG CTC TCT ATT CCA GAG GTG GTG AGG GGA        2502
Gln His Ile Tyr Lys Thr Leu Leu Ser Ile Pro Glu Val Val Arg Gly
        810                 815                 820

TGC AGA GAA CTA CAG GGA TTG CTG GAA TTT CTG AGC TAA GAAACTGAAA        2551
Cys Arg Glu Leu Gln Gly Leu Leu Glu Phe Leu Ser  *
    825                 830                 835

GCCAGAATCT GCTTCACCTC TTTTTACCTG CAATACCCCC TTACCCCAAT ACCAAGACCA    2611

ACTGGCATAG AGCCAACTGA GATAAATGCT ATTTAAATAA AGTGTATTTA ATGAAAACTC    2671

GTGCCGAATT CGGCACGAGC GGCACGAGCG GCACGAGCTG CAGCCATGTC TCTAGTGATC    2731

CCTGAAAAGT TCCAGCATAT TTTGCGAGTA CTCAACACCA ACATCGATGG GCGGCGGAAA    2791

ATAGCCTTTG CCATCACTGC CATTAAGGGT GTGGGCCGAA GATATGCTCA TGTGGTGTTG    2851

AGGAAAGCAG ACATTGACCT CACCAAGAGG GCGGAGAAC TCACTGAGGA TGAGGTGGAA     2911

CGTGTGATCA CCATTATGCA GAATCCACGC CAGTACAAGA TCCCAGACTG GTTCTTGAAC    2971

AGACAGAAGG ATGTAAAGGA TGGAAAATAC AGCCAGGTCC TAGCCAATGG TCTGGACAAC    3031

AAGCTCCGTG AAGACCTGGA GCGACTGAAG AAGATTCGGG CCCATAGAGG GCTGCGTCAC    3091

TTCTGGGGCC TTCGTGTCCG AGGCCAGCAC ACCAAGACCA CTGGCCGCCG TGGCCGCACC    3151

GTGGGTGTGT CCAAGAAGAA ATAAGTCTGT AGGCCTTGTC TGTTAATAAA TAGTTTATAT    3211

ACCAAAAAAA AAAAAAAAA ACTCGAGCAT GCATCTAGAG GGCCC                    3256

(2) INFORMATION FOR SEQ ID NO:4:

(i) SEQUENCE CHARACTERISTICS:
        (A) LENGTH: 835 amino acids
        (B) TYPE: amino acid
        (D) TOPOLOGY: linear (ii) MOLECULE TYPE: protein (xi) SEQUENCE DESCRIPTION: SEQ ID NO:4:

Ala Arg Glu Ser Leu Ser Leu Pro Ser Met Leu Arg Asp Ala Ala Ile
 1               5                  10                  15

Gly Thr Thr Pro Phe Ser Thr Cys Ser Val Gly Thr Trp Phe Thr Pro
                20                  25                  30

Ser Ala Pro Gln Glu Lys Ser Thr Asn Thr Ser Gln Thr Gly Leu Val
        35                  40                  45

Gly Thr Lys His Ser Thr Ser Glu Thr Glu Gln Leu Leu Cys Gly Arg
    50                  55                  60

Pro Pro Asp Leu Thr Ala Leu Ser Arg His Asp Leu Glu Asp Asn Leu
65                  70                  75                  80

Leu Ser Ser Leu Val Ile Leu Glu Val Leu Ser Arg Gln Leu Arg Asp
                85                  90                  95

Trp Lys Ser Gln Leu Ala Val Pro His Pro Glu Thr Gln Asp Ser Ser
            100                 105                 110

Thr Gln Thr Asp Thr Ser His Ser Gly Ile Thr Asn Lys Leu Gln His
        115                 120                 125

Leu Lys Glu Ser His Glu Met Gly Gln Ala Leu Gln Gln Ala Arg Asn
    130                 135                 140

Val Met Gln Ser Trp Val Leu Ile Ser Lys Glu Leu Ile Ser Leu Leu
145                 150                 155                 160

His Leu Ser Leu Leu His Leu Glu Glu Asp Lys Thr Thr Val Ser Gln
                165                 170                 175
```

```
Glu Ser Arg Arg Ala Glu Thr Leu Val Cys Cys Cys Phe Asp Leu Leu
            180                 185                 190

Lys Lys Leu Arg Ala Lys Leu Gln Ser Leu Lys Ala Glu Arg Glu Glu
            195                 200                 205

Ala Arg His Arg Glu Glu Met Ala Leu Arg Gly Lys Asp Ala Ala Glu
            210                 215                 220

Ile Val Leu Glu Ala Phe Cys Ala His Ala Ser Gln Arg Ile Ser Gln
225                 230                 235                 240

Leu Glu Gln Asp Leu Ala Ser Met Arg Glu Phe Arg Gly Leu Leu Lys
                245                 250                 255

Asp Ala Gln Thr Gln Leu Val Gly Leu His Ala Lys Gln Glu Glu Leu
            260                 265                 270

Val Gln Gln Thr Val Ser Leu Thr Ser Thr Leu Gln Gln Asp Trp Arg
            275                 280                 285

Ser Met Gln Leu Asp Tyr Thr Thr Trp Thr Ala Leu Leu Ser Arg Ser
            290                 295                 300

Arg Gln Leu Thr Glu Lys Leu Thr Val Lys Ser Gln Gln Ala Leu Gln
305                 310                 315                 320

Glu Arg Asp Val Ala Ile Glu Glu Lys Gln Glu Val Ser Arg Val Leu
                325                 330                 335

Glu Gln Val Ser Ala Gln Leu Glu Glu Cys Lys Gly Gln Thr Glu Gln
            340                 345                 350

Leu Glu Leu Glu Asn Ser Arg Leu Ala Thr Asp Leu Arg Ala Gln Leu
            355                 360                 365

Gln Ile Leu Ala Asn Met Asp Ser Gln Leu Lys Glu Leu Gln Ser Gln
370                 375                 380

His Thr His Cys Ala Gln Asp Leu Ala Met Lys Asp Glu Leu Phe Cys
385                 390                 395                 400

Gln Leu Thr Gln Ser Asn Glu Glu Gln Ala Ala Gln Trp Gln Lys Glu
                405                 410                 415

Glu Met Ala Leu Lys His Met Gln Ala Glu Leu Gln Gln Gln Gln Ala
            420                 425                 430

Val Leu Ala Lys Glu Val Arg Asp Leu Lys Glu Thr Leu Glu Phe Ala
            435                 440                 445

Asp Gln Glu Asn Gln Val Ala His Leu Glu Leu Gly Gln Val Glu Cys
450                 455                 460

Gln Leu Lys Thr Thr Leu Glu Val Leu Arg Glu Arg Ser Leu Gln Cys
465                 470                 475                 480

Glu Asn Leu Lys Asp Thr Val Glu Asn Leu Thr Ala Lys Leu Ala Ser
                485                 490                 495

Thr Ile Ala Asp Asn Gln Glu Gln Asp Leu Glu Lys Thr Arg Gln Tyr
            500                 505                 510

Ser Gln Lys Leu Arg Leu Leu Thr Glu Gln Leu Gln Ser Leu Thr Leu
            515                 520                 525

Phe Leu Gln Thr Lys Leu Lys Glu Lys Thr Gln Glu Thr Leu Leu
530                 535                 540

Leu Ser Thr Ala Cys Pro Pro Thr Gln Glu His Pro Leu Pro Asn Asp
545                 550                 555                 560

Arg Thr Phe Leu Gly Ser Ile Leu Thr Ala Val Ala Asp Glu Glu Pro
                565                 570                 575

Glu Ser Thr Pro Val Pro Leu Leu Gly Ser Asp Lys Ser Ala Phe Thr
            580                 585                 590

Arg Val Ala Ser Met Val Ser Leu Gln Pro Ala Glu Thr Pro Gly Met
```

```
                     595                600                     605

Glu Glu Ser Leu Ala Glu Met Ser Ile Met Thr Thr Glu Leu Gln Ser
    610                 615                 620

Leu Cys Ser Leu Leu Gln Glu Ser Lys Glu Glu Ala Ile Arg Thr Leu
625                 630                 635                 640

Gln Arg Lys Ile Cys Glu Leu Gln Val Arg Leu Gln Ala Gln Glu Glu
                645                 650                 655

Gln His Gln Glu Val Gln Lys Ala Lys Glu Ala Asp Ile Glu Lys Leu
                660                 665                 670

Asn Gln Ala Leu Cys Leu Arg Tyr Lys Asn Glu Lys Glu Leu Gln Glu
            675                 680                 685

Val Ile Gln Gln Gln Asn Glu Lys Ile Leu Gln Ile Asp Lys Ser
690                 695                 700

Gly Glu Leu Ile Ser Leu Arg Glu Glu Val Thr His Leu Thr Arg Ser
705                 710                 715                 720

Leu Arg Arg Ala Glu Thr Glu Thr Lys Val Leu Gln Glu Ala Leu Ala
                725                 730                 735

Gly Gln Leu Asp Ser Asn Cys Gln Pro Met Ala Thr Asn Trp Ile Gln
            740                 745                 750

Glu Lys Val Trp Leu Ser Gln Glu Val Asp Lys Leu Arg Val Met Phe
        755                 760                 765

Leu Glu Met Lys Asn Glu Lys Glu Lys Leu Met Ile Lys Phe Gln Ser
770                 775                 780

His Arg Asn Ile Leu Glu Glu Asn Leu Arg Arg Ser Asp Lys Glu Leu
785                 790                 795                 800

Glu Lys Leu Asp Asp Ile Val Gln His Ile Tyr Lys Thr Leu Leu Ser
                805                 810                 815

Ile Pro Glu Val Val Arg Gly Cys Arg Glu Leu Gln Gly Leu Leu Glu
            820                 825                 830

Phe Leu Ser
        835

(2) INFORMATION FOR SEQ ID NO:5:

(i) SEQUENCE CHARACTERISTICS:
        (A) LENGTH: 1191 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 34..1191

(xi) SEQUENCE DESCRIPTION: SEQ ID NO:5:

GAACTAGTGG ATCCCCCGGG CTGCAGGAAT TCG GCA CGA GGC GGC GCC GAA GAG         54
                                    Ala Arg Gly Gly Ala Glu Glu
                                                    1               5

GCG ACT GAG GCC GGA CGG GGC GGA CGG CGA CGC AGC CCG CGG CAG AAG        102
Ala Thr Glu Ala Gly Arg Gly Gly Arg Arg Arg Ser Pro Arg Gln Lys
        10                  15                  20

TTT GAA ATT GGC ACA ATG GAA GAA GCT GGA ATT TGT GGG CTA GGG GTG        150
Phe Glu Ile Gly Thr Met Glu Glu Ala Gly Ile Cys Gly Leu Gly Val
    25                  30                  35

AAA GCA GAT ATG TTG TGT AAC TCT CAA TCA AAT GAT ATT CTT CAA CAT        198
Lys Ala Asp Met Leu Cys Asn Ser Gln Ser Asn Asp Ile Leu Gln His
40                  45                  50                  55
```

```
CAA GGC TCA AAT TGT GGT GGC ACA AGT AAC AAG CAT TCA TTG GAA GAG       246
Gln Gly Ser Asn Cys Gly Gly Thr Ser Asn Lys His Ser Leu Glu Glu
                60                  65                  70

GAT GAA GGC AGT GAC TTT ATA ACA GAG AAC AGG AAT TTG GTG AGC CCA       294
Asp Glu Gly Ser Asp Phe Ile Thr Glu Asn Arg Asn Leu Val Ser Pro
        75                  80                  85

GCA TAC TGC ACG CAA GAA TCA AGA GAG GAA ATC CCT GGG GGA GAA GCT       342
Ala Tyr Cys Thr Gln Glu Ser Arg Glu Glu Ile Pro Gly Gly Glu Ala
                90                  95                 100

CGA ACA GAT CCC CCT GAT GGT CAG CAA GAT TCA GAG TGC AAC AGG AAC       390
Arg Thr Asp Pro Pro Asp Gly Gln Gln Asp Ser Glu Cys Asn Arg Asn
        105                 110                 115

AAA GAA AAA ACT TTA GGA AAA GAA GTT TTA TTA CTG ATG CAA GCC CTA       438
Lys Glu Lys Thr Leu Gly Lys Glu Val Leu Leu Leu Met Gln Ala Leu
120                 125                 130                 135

AAC ACC CTT TCA ACC CCA GAG GAG AAG CTG GCA GCT CTC TGT AAG AAA       486
Asn Thr Leu Ser Thr Pro Glu Glu Lys Leu Ala Ala Leu Cys Lys Lys
            140                 145                 150

TAT GCT GAT CTT CTG GAG GAG AGC AGG AGT GTT CAG AAG CAA ATG AAG       534
Tyr Ala Asp Leu Leu Glu Glu Ser Arg Ser Val Gln Lys Gln Met Lys
                155                 160                 165

ATC CTG CAG AAG AAG CAA GCC CAG ATT GTG AAA GAG AAA GTT CAC TTG       582
Ile Leu Gln Lys Lys Gln Ala Gln Ile Val Lys Glu Lys Val His Leu
        170                 175                 180

CAG AGT GAA CAT AGC AAG GCT ATC TTG GCA AGA AGC AAG CTA GAA TCT       630
Gln Ser Glu His Ser Lys Ala Ile Leu Ala Arg Ser Lys Leu Glu Ser
185                 190                 195

CTT TGC AGA GAA CTT CAG CGT CAC AAT AAG ACG TTA AAG GAG GAA AAT       678
Leu Cys Arg Glu Leu Gln Arg His Asn Lys Thr Leu Lys Glu Glu Asn
200                 205                 210                 215

ATG CAG CAG GCA CGA GAG GAA GAA CGA CGT ATA GAA GCA ACT GCA           726
Met Gln Gln Ala Arg Glu Glu Glu Arg Arg Ile Glu Ala Thr Ala
                220                 225                 230

CAT TTC CAG ATT ACC TTA AAT GAA ATT CAA GCC CAG CTG GAG CAG CAT       774
His Phe Gln Ile Thr Leu Asn Glu Ile Gln Ala Gln Leu Glu Gln His
            235                 240                 245

GAC ATC CAC AAC GCC AAA CTC CGA CAG GAA AAC ATT GAG CTG GGG GAG       822
Asp Ile His Asn Ala Lys Leu Arg Gln Glu Asn Ile Glu Leu Gly Glu
        250                 255                 260

AAG CTA AAG AAG CTC ATC GAA CAG TAC GCA CTG AGG GAA GAG CAC ATT       870
Lys Leu Lys Lys Leu Ile Glu Gln Tyr Ala Leu Arg Glu Glu His Ile
265                 270                 275

GAT AAG GTG TTC AAA CAT AAG GAA CTG CAA CAG CAG CTC GTG GAT GCC       918
Asp Lys Val Phe Lys His Lys Glu Leu Gln Gln Gln Leu Val Asp Ala
280                 285                 290                 295

AAA CTG CAG CAA ACG ACA CAA CTG ATA AAA GAA GCT GAT GAA AAA CAT       966
Lys Leu Gln Gln Thr Thr Gln Leu Ile Lys Glu Ala Asp Glu Lys His
                300                 305                 310

CAG AGA GAG AGA GAG TTT TTA TTA AAA GAA GCG ACA GAA TCG AGG CAC      1014
Gln Arg Glu Arg Glu Phe Leu Leu Lys Glu Ala Thr Glu Ser Arg His
            315                 320                 325

AAA TAC GAA CAA ATG AAA CAG CAA GAA GTA CAA CTA AAA CAG CAG CTT      1062
Lys Tyr Glu Gln Met Lys Gln Gln Glu Val Gln Leu Lys Gln Gln Leu
        330                 335                 340

TCT CTT TAT ATG GAT AAG TTT GAA GAA TTC CAG ACT ACC ATG GCA AAA      1110
Ser Leu Tyr Met Asp Lys Phe Glu Glu Phe Gln Thr Thr Met Ala Lys
345                 350                 355

AGC AAT GAA CTG TTT ACA ACC TTC AGA CAG GAA ATG GAA AAG ATG ACA      1158
Ser Asn Glu Leu Phe Thr Thr Phe Arg Gln Glu Met Glu Lys Met Thr
360                 365                 370                 375
```

```
AAG AAA ATT AAA AAA AAA AAA AAA CTC GAG                              1191
Lys Lys Ile Lys Lys Lys Lys Lys Leu Glu
            380                 385
```

(2) INFORMATION FOR SEQ ID NO:6:

(i) SEQUENCE CHARACTERISTICS:
        (A) LENGTH: 386 amino acids
        (B) TYPE: amino acid
        (D) TOPOLOGY: linear (ii) MOLECULE TYPE: protein (xi) SEQUENCE DESCRIPTION: SEQ ID NO:6:

```
Ala Arg Gly Gly Ala Glu Glu Ala Thr Glu Ala Gly Arg Gly Arg
 1               5                  10                  15

Arg Arg Ser Pro Arg Gln Lys Phe Glu Ile Gly Thr Met Glu Glu Ala
            20                  25                  30

Gly Ile Cys Gly Leu Gly Val Lys Ala Asp Met Leu Cys Asn Ser Gln
        35                  40                  45

Ser Asn Asp Ile Leu Gln His Gln Gly Ser Asn Cys Gly Gly Thr Ser
    50                  55                  60

Asn Lys His Ser Leu Glu Glu Asp Glu Gly Ser Asp Phe Ile Thr Glu
65                  70                  75                  80

Asn Arg Asn Leu Val Ser Pro Ala Tyr Cys Thr Gln Glu Ser Arg Glu
                85                  90                  95

Glu Ile Pro Gly Gly Glu Ala Arg Thr Asp Pro Pro Asp Gly Gln Gln
            100                 105                 110

Asp Ser Glu Cys Asn Arg Asn Lys Glu Lys Thr Leu Gly Lys Glu Val
        115                 120                 125

Leu Leu Leu Met Gln Ala Leu Asn Thr Leu Ser Thr Pro Glu Glu Lys
    130                 135                 140

Leu Ala Ala Leu Cys Lys Lys Tyr Ala Asp Leu Leu Glu Glu Ser Arg
145                 150                 155                 160

Ser Val Gln Lys Gln Met Lys Ile Leu Gln Lys Lys Gln Ala Gln Ile
                165                 170                 175

Val Lys Glu Lys Val His Leu Gln Ser Glu His Ser Lys Ala Ile Leu
            180                 185                 190

Ala Arg Ser Lys Leu Glu Ser Leu Cys Arg Glu Leu Gln Arg His Asn
        195                 200                 205

Lys Thr Leu Lys Glu Glu Asn Met Gln Gln Ala Arg Glu Glu Glu Glu
    210                 215                 220

Arg Arg Ile Glu Ala Thr Ala His Phe Gln Ile Thr Leu Asn Glu Ile
225                 230                 235                 240

Gln Ala Gln Leu Glu Gln His Asp Ile His Asn Ala Lys Leu Arg Gln
                245                 250                 255

Glu Asn Ile Glu Leu Gly Glu Lys Leu Lys Lys Leu Ile Glu Gln Tyr
            260                 265                 270

Ala Leu Arg Glu Glu His Ile Asp Lys Val Phe Lys His Lys Glu Leu
        275                 280                 285

Gln Gln Gln Leu Val Asp Ala Lys Leu Gln Gln Thr Thr Gln Leu Ile
    290                 295                 300

Lys Glu Ala Asp Glu Lys His Gln Arg Glu Arg Glu Phe Leu Leu Lys
305                 310                 315                 320

Glu Ala Thr Glu Ser Arg His Lys Tyr Glu Gln Met Lys Gln Gln Glu
                325                 330                 335

Val Gln Leu Lys Gln Gln Leu Ser Leu Tyr Met Asp Lys Phe Glu Glu
```

```
                    340                 345                 350
Phe Gln Thr Thr Met Ala Lys Ser Asn Glu Leu Phe Thr Thr Phe Arg
            355                 360                 365

Gln Glu Met Glu Lys Met Thr Lys Lys Ile Lys Lys Lys Lys Lys Lys
    370                 375                 380

Leu Glu
385
```